(12) United States Patent
Dufour-Schroif et al.

(10) Patent No.: US 8,765,799 B2
(45) Date of Patent: Jul. 1, 2014

(54) STREPTOSPIROLE DERIVATIVES

(75) Inventors: Cosima Dufour-Schroif, Paris (FR);
Joachim Wink, Frankfurt am Main (DE); Martin Gerlitz, Frankfurt am Main (DE); Hélène Olivan, Paris (FR); Michael Kurz, Frankfurt am Main (DE)

(73) Assignee: Sanofi, Paris (FR)

( * ) Notice: Subject to any disclaimer, the term of this patent is extended or adjusted under 35 U.S.C. 154(b) by 531 days.

(21) Appl. No.: 13/056,751

(22) PCT Filed: Jul. 16, 2009

(86) PCT No.: PCT/EP2009/005155
§ 371 (c)(1),
(2), (4) Date: Aug. 17, 2011

(87) PCT Pub. No.: WO2010/012381
PCT Pub. Date: Feb. 4, 2010

(65) Prior Publication Data
US 2011/0295009 A1 Dec. 1, 2011

(30) Foreign Application Priority Data
Jul. 31, 2008 (EP) ..................................... 08167138

(51) Int. Cl.
*A61K 31/407* (2006.01)
*C07D 491/107* (2006.01)
*C07D 498/10* (2006.01)

(52) U.S. Cl.
CPC .................................... *C07D 498/10* (2013.01)
USPC .......................................... 514/409; 548/430

(58) Field of Classification Search
USPC ......................................................... 548/430
See application file for complete search history.

(56) References Cited

FOREIGN PATENT DOCUMENTS

WO    WO 03/029213 A1    4/2003
WO    WO 2005/121148 A2    12/2005

OTHER PUBLICATIONS

Staph Infection [online] {retrieved on Apr. 10, 2008 from the Internet} {URL: http://www.medicinenet.com/script/main/art.asp?articlekey=1991&pf=3&page2}.*
Pseudomonas [online] {retrieved on Apr. 11, 2008 from the Internet} {URL: http://www.merck.com/m mhe/sect 17/ch1 90/ch 1900.html#sec1 7-ch 190-ch 1900-262}.*
Salmonellosis [online] [retrieved on Feb. 27, 2009] and retrieved from URL; http://www.cdc.gov/nczved/dfbmed/disease_listing/salmonellosis_gi.html#4.*
Shavaleeva, G.A. et al., "Reactions of 2,3,5-Trichloro-4,4-ethylenedioxy-2-cyclopentenone with Some Ambident Nucleophiles. Sterically Loaded Functionalized 6-Azabicyclo[3.1.0]hex-5-enes," Russian Journal of Organic Chemistry (2004), vol. 40, pp. 1521-1525.
Dolle, Roland E. et al., "Synthesis of Zymosterol, Fecosterol, and Related Biosynthetic Sterol Intermediates[1,2]," Journal of the American Chemical Society (1989) vol. 111, pp. 278-284.
Bishop, Michael J. et al., "3-($\alpha$R)-$\alpha$-((2S,5R)-4-Allyl-2,5-dimethyl-1-piperazinyl)-3-hydroxybenzyl)-N-alkyl-N-arylbenzamides: Potent, Non-Peptidic Agonists of Both the $\mu$ and $\delta$ Opioid Receptors," Journal of Medicinal Chemistry (2003), vol. 46, pp. 623-633.
Gilleron, Pauline et al., "Design, synthesis and biological evaluation of substituted dioxodibenzothiazepines and dibenzocycloheptanes as farnesyltransferase inhibitors," Bioorganic & Medicinal Chemistry Letters (2007), vol. 17, pp. 5465-5471.
Baquero, Fernando, "Gram-positive resistance: challenge for the development of new antibiotics," Journal of Antimicrobial Chemotherapy (1997), vol. 39, pp. 1-6.
Kunieda, Michio et al., "Self-Aggregation of Synthetic Zinc Chlorins Possessing a 13-Ester-Carbonyl Group as Chlorosomal Chlorophyll Models," European Journal of Organic Chemistry (2006), pp. 2352-2361.
Kweon, Deok-Heon et al., "Arenesulfonylheterocycles (I): Synthesis and Reactions of 2-Benzenesulfonyl-4,5-dichloropyridazin-3-ones with Amines," Journal of Heterocyclic Chemistry (2002), vol. 39, pp. 203-211.
Booker-Milburn, Kevin I. et al., "Rapid Access to Azepine-Fused Oxetanols from Alkoxy-Substituted Maleimides," Organic Letters (2004), vol. 6, pp. 1481-1484.
Remington's Pharmaceutical Sciences, 17th Edition (1985), p. 1418.

(Continued)

*Primary Examiner* — Shawquia Young
(74) *Attorney, Agent, or Firm* — Scully, Scott, Murphy & Presser, P.C.

(57) ABSTRACT

The invention relates to streptospirole derivatives of the general formula (I), wherein $R_1, R_2, R_3, X_1, X_2, Y_1$ and $Y_2$ are as defined herein, a process for the preparation of said compounds by fermenting the microorganism *Streptomyces* sp. ST 108140 (DSM 19369) and optionally derivatizing the compounds produced by said microorganism, a pharmaceutical composition comprising at least one compound of the formula (I), and the use of a compound of the formula (I) for the preparation of a medicament for the treatment and/or prophylaxis of bacterial infections.

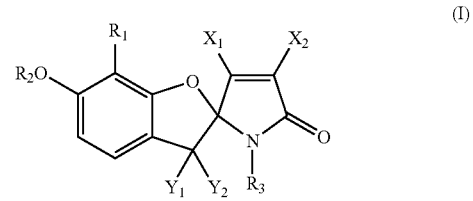

(I)

18 Claims, No Drawings

(56) References Cited

OTHER PUBLICATIONS

Stolp, Heinz, "Microbial Ecology," Cambridge University Press (1988), p. 180.

Brock, Thomas D. et al., Biology of Microorganisms 4$^{th}$ Edition (1984), pp. 304-315.

Brock, Thomas D. et al., Biology of Microorganisms 4$^{th}$ Edition (1984), pp. 238-247.

Tenover, Fred C. et al., "Increasing Resistance to Vancomycin and Other Glycopeptides in *Staphylococcus aureus*," Emerging Infectious Diseases (2001), vol. 7, pp. 327-332.

International Search Report dated Nov. 16, 2009.

European Search Report Dec. 16, 2008.

* cited by examiner

STREPTOSPIROLE DERIVATIVES

The incidence of infections caused by multidrug-resistant Gram-positive bacteria is increasing despite advances in antibacterial therapy over the last decades. As the pathogens causing these infections are frequently resistant to most currently available antibacterials, they are extremely difficult to treat. Almost all bacteria treated with antibiotics have developed at least some degree of resistance against these drugs (F. Baquero, J. Antimicrob. Chemother. 1977, 39, 1-6). The emergence of high levels of penicillin resistance followed by the evolvement and spread of strains resistant to the semisynthetic penicillins (methicillin, nafcillin and oxacillin), macrolides, tetracyclines, aminoglycosides and glycopeptides (vancomycin e.g.) has made therapy of staphylococcal diseases a global challenge. In many countries, an increasing number of clinical isolates of multiresistant *Staphylococcus aureus* strains have been observed and the pathogenic potential in nocosomial and community acquired infections is well known (F. C. Tenover et al., Emer. Infec. Dis. 2001, 7, 327-332).

It has now been found that the microorganism strain *Streptomyces* sp. ST 108140 (DSM 19369) produces novel compounds that have a novel chemical skeletal structure, named streptospirole, and that inhibit the growth of Gram-positive bacteria at low concentrations and are consequently suitable to be used for the treatment and/or prophylaxis of bacterial infections.

The present invention relates to a compound of the formula (I),

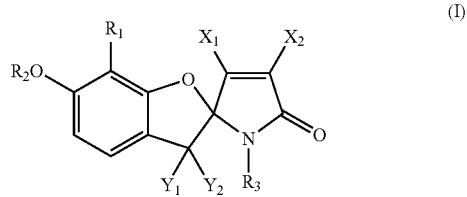

(I)

wherein
$R_1$ is $(C_6-C_7)$alkyl,
$R_2$ is H, $(C_1-C_6)$alkyl or $(C_1-C_6)$alkylene-OH,
$R_3$ is H or $(C_1-C_6)$alkyl,
$X_1$ is halogen, O—$(C_1-C_6)$alkyl, NH[$(C_1-C_6)$alkyl], NH[$(C_1-C_4)$alkylene-$(C_6-C_{10})$-aryl], NH[$(C_1-C_4)$alkylene-$(C_6-C_{10})$-heteroaryl], or S—$(C_1-C_4)$alkylene-N[$(C_1-C_4)$alkyl]$_2$,
$X_2$ is halogen, and
$Y_1$ and $Y_2$ are independently of each other H; OH; NH[$(C_1-C_6)$alkyl]; NH[$(C_1-C_4)$alkylene-$(C_6-C_{10})$-aryl] wherein the $(C_6-C_{10})$-aryl group is optionally substituted by halogen; NH[$(C_1-C_4)$alkylene-$(C_6-C_{10})$-heteroaryl]; a saturated or unsaturated heterocyclic ring system containing 5 to 6 ring atoms optionally substituted by $(C_1-C_6)$alkyl wherein one or 2 ring atoms are N, O or S; or $Y_1$ and $Y_2$ together are =O,
or a physiologically tolerated salt of a compound of the formula (I).

Alkyl and alkylene groups are defined as straight chain or branched alkyl group containing the number of carbon atoms indicated.

$(C_6-C_{10})$-aryl is defined as an aromatic hydrocarbon having 6 to 10 carbon atoms. Examples of aryl groups include phenyl and naphthyl.

$(C_6-C_{10})$-heteroaryl is defined as an aryl group wherein one or more carbon atom of the aromatic hydrocarbon has been replaced with a heteroatom wherein the term "heteroatom" includes oxygen, nitrogen, sulfur, and phosphorus. Examples of heteroaryl groups include furan, thiophene, benzothiophene, pyrrole, thiazole, pyridine, pyrimidine, pyrazine, benzofuran, indole, coumarin, quinoline, isoquinoline, and naphthyridine.

Saturated or unsaturated heterocyclic ring system containing 5 to 6 ring atoms are e.g. furan, 2H-pyran, 4H-pyran, thiophene, parathiazine, pyrrole, pyrrolidine, pyrazole, pyrazolidine, imidazole, imidazoline, imidazolidine, pyridine, pyrazine, piperazine, piperidine, pyrimidine or morpholine.

$R_2$ is preferably H or $(C_1-C_4)$alkyl or $(C_1-C_4)$alkylene-OH, more preferred H or methyl or ethylene-OH, most preferred H.

$R_3$ is preferably H or $(C_1-C_4)$alkyl, more preferred methyl.
$X_1$ is preferably Cl, Br, O—$(C_1-C_4)$alkyl, NH[$(C_1-C_4)$alkyl], NH[$(C_1-C_4)$alkylene-pyridyl], or S—$(C_1-C_4)$alkylene-N[$(C_1-C_4)$alkyl]$_2$, more preferred Cl or Br, most preferred Cl.

$X_2$ is preferably Cl or Br, most preferred Cl.
More preferred, $X_1$ and $X_2$ are both Cl.
$Y_1$ and $Y_2$ are preferably independently of each other selected from the group consisting of H; OH; NH[$(C_1-C_6)$alkyl]; NH—$CH_2$-phenyl wherein the phenyl group is optionally substituted by halogen, preferably by fluorine; a saturated heterocyclic ring system containing 5 to 6 ring atoms optionally substituted by $(C_1-C_6)$alkyl, more preferred piperazine, piperidine, morpholine or N-methyl morpholine.

More preferred, $Y_1$ and $Y_2$ are together =O.
Further preferred, the invention relates to a compound of the formula (I) wherein
$R_1$ is $(C_6-C_7)$alkyl,
$R_2$ is H, $(C_1-C_4)$alkyl or $(C_1-C_4)$alkylene-OH,
$R_3$ is H or $(C_1-C_4)$alkyl,
$X_1$ is halogen, O—$(C_1-C_4)$alkyl, NH[$(C_1-C_6)$alkyl], NH[$(C_1-C_4)$alkylene-heteroaryl] or S—$(C_1-C_4)$alkylene-N[$(C_1-C_4)$alkyl]$_2$, more preferred Cl or Br, most preferred Cl.
$X_2$ is halogen, preferably Cl or Br, and
$Y_1$ and $Y_2$ are preferably independently of each other a group selected from H; OH;
NH[$(C_1-C_6)$alkyl]; NH—$CH_2$-phenyl wherein the phenyl group is optionally substituted by halogen; a saturated heterocyclic ring system containing 5 to 6 ring atoms optionally substituted by $(C_1-C_6)$alkyl; or $Y_1$ and $Y_2$ together are =O,
or a physiologically tolerated salt of a compound of the formula (I).

Further preferred, the invention relates to a compound of the formula (I) wherein
$R_1$ is $(C_6-C_7)$alkyl,
$R_2$ is H, $(C_1-C_4)$alkyl or $(C_1-C_4)$alkylene-OH,
$R_3$ is $(C_1-C_4)$alkyl, preferably methyl,
$X_1$ is Cl, Br, NH[$(C_1-C_4)$alkyl], NH[$(C_1-C_4)$alkylene-pyridyl], or S—$(C_1-C_4)$alkylene-N[$(C_1-C_4)$alkyl]$_2$,
$X_2$ is Cl or Br, and
$Y_1$ and $Y_2$ are independently of each other H or OH, or $Y_1$ and $Y_2$ are together =O,
or a physiologically tolerated salt thereof.

Further preferred, the invention relates to a compound of the formula (I) wherein
$R_1$ is $(C_6-C_7)$alkyl,
$R_2$ is H, $(C_1-C_2)$alkyl or $(C_1-C_2)$alkylene-OH,
$R_3$ is methyl,
$X_1$ is Cl, Br, NH[butyl], NH[$CH_2$-pyridyl], or S-ethylene-N[$(C_1-C_2)$alkyl]$_2$, $X_2$ is an Cl or Br, and $Y_1$ and $Y_2$ are independently of each other H or OH, or $Y_1$ and $Y_2$ are together =O, or a physiologically tolerated salt thereof.

Further preferred, the invention relates to a compound of the formula (I) wherein $R_1$ is ($C_6$-$C_7$)alkyl, $R_2$ is H, $R_3$ is methyl, $X_1$ and $X_2$ are independently of each other Cl or Br, $Y_1$ and $Y_2$ together are =O, or a physiologically tolerated salt thereof.

Further preferred, the invention relates to a compound of the formula (I) wherein $R_1$ is ($C_6$-$C_7$)alkyl, $R_2$ is H, $R_3$ is methyl, $X_1$ and $X_2$ are both Cl, $Y_1$ and $Y_2$ together are =O, or a physiologically tolerated salt thereof.

In the compound of the formula (I) as described above, $R_1$ is preferably n-hexyl, 4-methyl-pentyl, n-heptyl and 4-methyl-hexyl.

Examples of preferred compounds of the formula (I) are as follows:

(II)

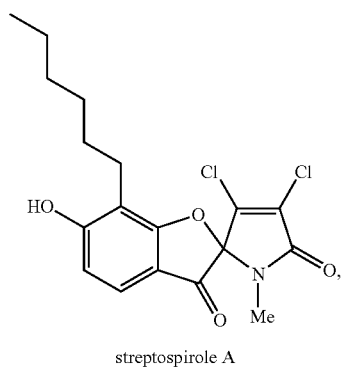

streptospirole A (III)

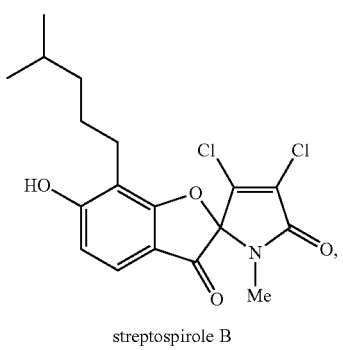

streptospirole B (IV)

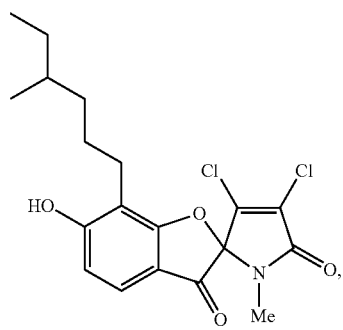

streptospirole C (VI)

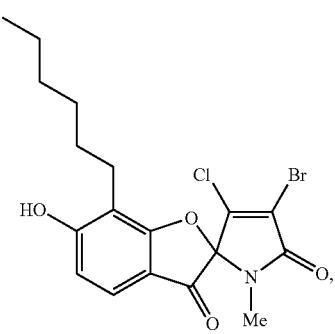

streptospirole D (VII)

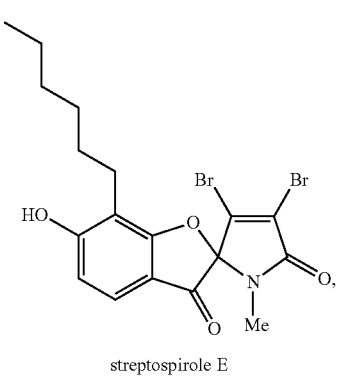

streptospirole E (VIII)

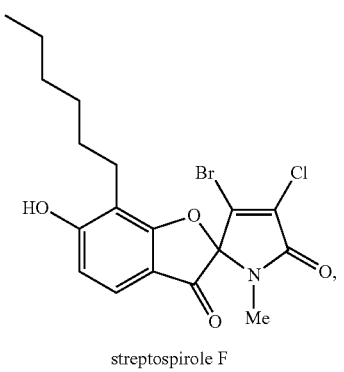

streptospirole F

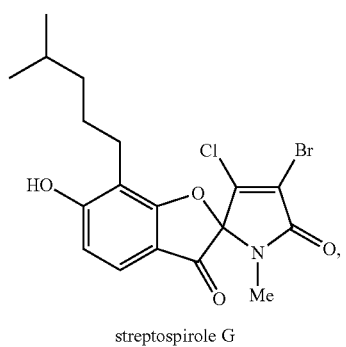
streptospirole G
(IX)
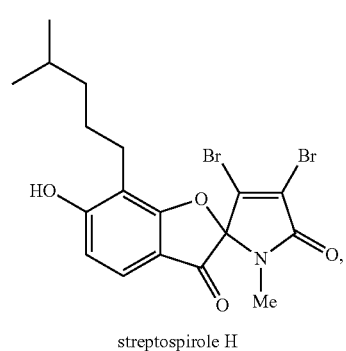
streptospirole H
(X)
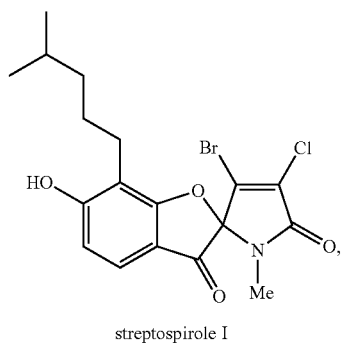
streptospirole I
(XI)
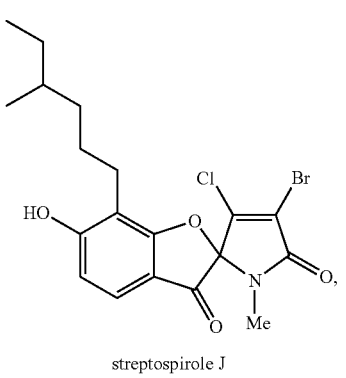
streptospirole J
(XII)
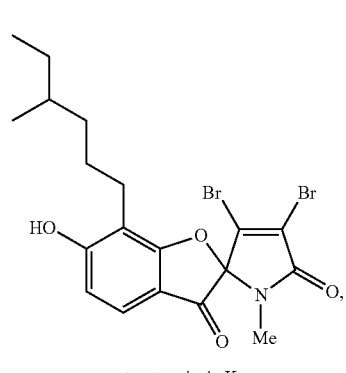
streptospirole K
(XIII)
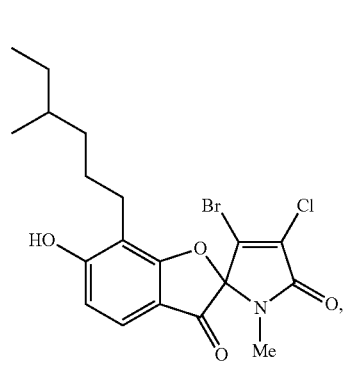
streptospirole L
(XIV)
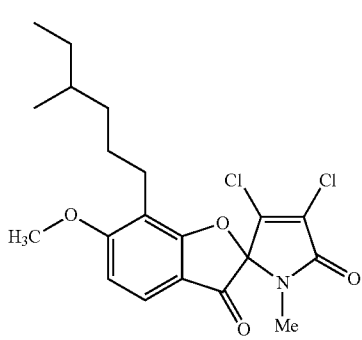
(XVI)
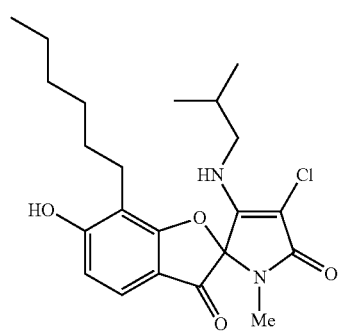
(XVII)

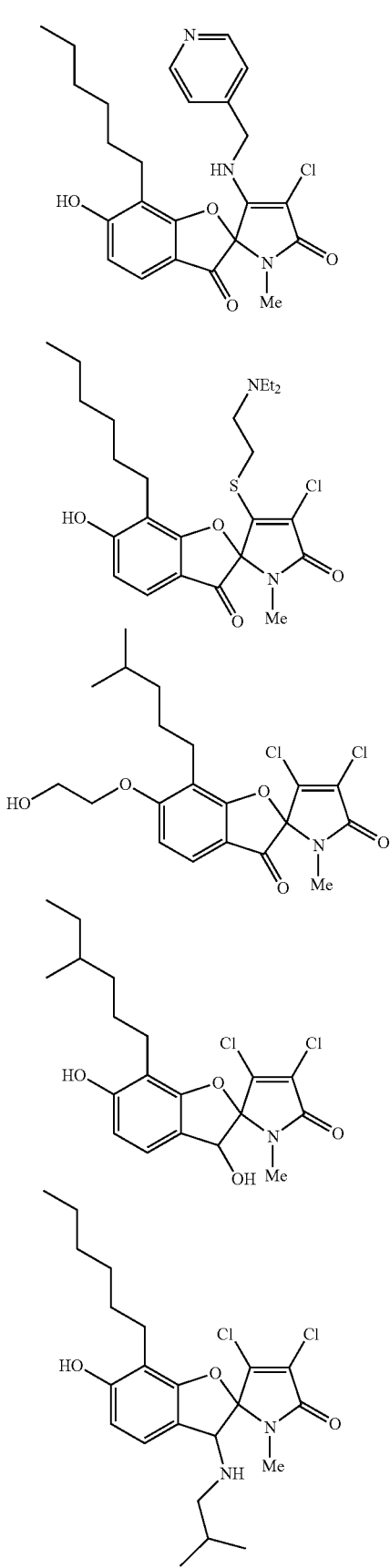
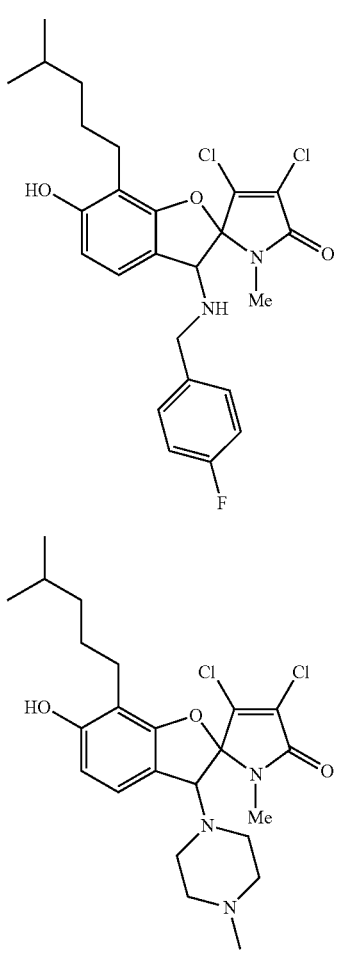
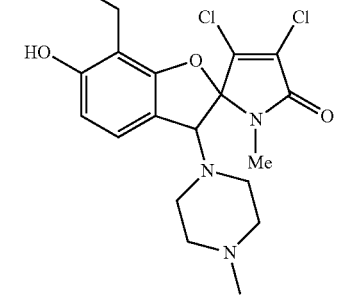
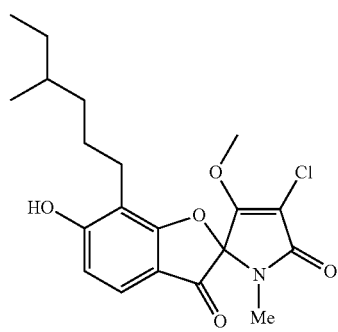

The present invention furthermore relates to all obvious chemical equivalents of the compounds of the formula (I). These equivalents are compounds which exhibit only a slight structural difference, and have the same pharmacological effect, or which are converted into the compounds according to the invention under mild conditions. Said equivalents also include, for example, reduction products, oxidation products, esters, ethers, acetals or amides of a compound of the formula (I). Said equivalents can prepare by the skilled person using standard methods.

Unless otherwise indicated, the chiral centers in the compounds of the formula (I) can be presented in the R configuration or in the S configuration. The invention relates to the pure enantiomers or diastereomers, and to mixtures thereof.

Physiologically tolerated salts of compounds of the formula (I) are understood as being both their organic salts and their inorganic salts, as are described in Remington's Pharmaceutical Sciences (17th edition, page 1418 (1985)). Because of their physical and chemical stability and their solubility, sodium, potassium, calcium and ammonium salts are preferred, inter alia, for acidic groups; salts of hydrochloric acid, sulfuric acid or phosphoric acid, or of carboxylic acids or sulfonic acids, such as acetic acid, citric acid, benzoic acid, maleic acid, fumaric acid, tartaric acid and p-toluenesulfonic acid, are preferred, inter alia, for basic groups.

The invention further relates to a process for preparing a compound of the formula (I) or a physiologically tolerated salt of a compound of the formula (I) wherein $R_1$ is $(C_6-C_7)$alkyl, $R_2$ is H, $(C_1-C_6)$alkyl or $(C_1-C_6)$alkylene-OH, $R_3$ is H or $(C_1-C_6)$alkyl, $X_1$ is halogen, O—$(C_1-C_6)$alkyl, NH[$(C_1-C_6)$alkyl], NH[$(C_1-C_4)$alkylene-$(C_6-C_{10})$-aryl], NH[$(C_1-C_4)$alkylene-$(C_6-C_{10})$-heteroaryl], or S—$(C_1-C_4)$alkylene-N[$(C_1-C_4)$alkyl]$_2$, $X_2$ is halogen, and $Y_1$ and $Y_2$ are independently of each other H; OH; NH[$(C_1-C_6)$alkyl]; NH[$(C_1-C_4)$alkylene-$(C_6-C_{10})$-aryl] wherein the $(C_6-C_{10})$-aryl group is optionally substituted by halogen; N[$(C_1-C_4)$alkylene-$(C_6-C_{10})$-heteroaryl]; a saturated or unsaturated heterocyclic ring system containing 5 to 6 ring atoms optionally substituted by $(C_1-C_6)$alkyl wherein one or 2 ring atoms are N, O or S; or $Y_1$ and $Y_2$ together are =O, or a physiologically tolerated salt of a compound of the formula (I), which comprises 1. fermenting the strain *Streptomyces* sp. ST 108140 (DSM 19369), or one of its variants and/or mutants, under suitable conditions in a culture medium until one or more of the compounds of the formula (I) accrue(s) in the culture medium,
2. isolating a compound of the formula (I) from the culture medium, and
3. derivatizing the isolated compound of the formula (I) to a compound of the formula (I), where appropriate, and/or, where appropriate, converting the isolated or derivatized compound into a physiologically tolerated salt of a compound of the formula (I).

In the process for preparing a compound of the formula (I), the compound of the formula (I) is preferably a compound of the formulae (II), (III), (IV), (VI), (VII), (VIII), (IX), (X), (XI), (XII), (XIII), (XIV) or a mixture thereof, more preferred a compound of the formulae (II), (III) or (IV).

The culture medium is a nutrient solution or a solid medium containing at least one customary carbon source and nitrogen source as well as the customary inorganic salts. If chloride salt is present in the culture medium, the strain *Streptomyces* sp. ST 108140 (DSM 19369) produces a compound of the formula (I) in which $X_1$ and/or $X_2$ can be Cl as a result of incorporation. Likewise, if bromide salt is present in the culture medium, the strain *Streptomyces* sp. ST 108140 (DSM 19369) produces a compound of the formula (I) in which $X_1$ and/or $X_2$ can be Br as a result of incorporation.

The process according to the invention can be used for fermenting on a laboratory scale (milliliter to liter scale) and for fermenting on an industrial scale (cubic meter scale).

Suitable carbon sources for the fermentation are assimilable carbohydrates and sugar alcohols, such as glucose, lactose, sucrose or D-mannitol, as well as carbohydrate-containing natural products, such as malt extract or yeast extract. Examples of nitrogen-containing nutrients are amino acids, peptides and proteins and also their breakdown products, for example casein, peptones or tryptones; meat extracts; yeast extracts; gluten; ground seeds, for example from corn, wheat, beans, soy or the cotton plant; distillation residues from producing alcohol; meat meals; yeast extracts; ammonium salts; nitrates. Preference is given to the nitrogen source being one or more peptide(s) which has/have been obtained synthetically or biosynthetically. Examples of inorganic salts are chlorides, carbonates, sulfates or phosphates of the alkali metals, the alkaline earth metals, iron, zinc, cobalt and manganese. Examples of trace elements are cobalt and manganese.

Conditions which are suitable for forming the streptospiroles according to the invention are as follows: the streptospiroles according to the invention are preferably formed in a culture medium which contains from 0.5 to 10.0%, preferably from 1.0 to 5.0%, yeast extract; from 5.0 to 15.0%, preferably from 7.0 to 12.0%, malt extract; from 0.5 to 10.0%, preferably from 1.0 to 5.0%, glucose. The percentage values which are given are in each case based on the weight of the total nutrient solution.

The microorganism is cultured aerobically, that is, for example, submerged while being shaken or stirred in shaking flasks or fermenters, or on solid medium, where appropriate while air or oxygen is being passed in. The microorganism can be cultured in a temperature range of from about 18 to 35° C., preferably at from about 25 to 32° C., in particular at from 27 to 30° C. The pH range should be between 4 and 10, preferably between 6.5 and 7.5. The microorganism is generally cultured under these conditions for a period of from 2 to 10 days, preferably of from 72 to 168 hours. The microorganism is advantageously cultured in several steps, i.e. one or more preliminary cultures are initially prepared in a liquid nutrient medium, with these preliminary cultures then being inoculated into the actual production medium, i.e. the main culture, for example in a ratio by volume of from 1:10 to 1:100. The preliminary culture is obtained, for example, by inoculating the strain, in the form of vegetative cells or spores, into a nutrient solution and allowing it to grow for from about 20 to 120 hours, preferably for from 48 to 96 hours. Vegetative cells and/or spores can be obtained, for example, by allowing the strain to grow for from about 1 to 15 days, preferably for from 4 to 10 days, on a solid or liquid nutrient substrate, for example yeast malt agar or oatmeal agar.

An isolate of the microorganism ST 108140 was deposited at the Deutschen Sammlung von Mikroorganismen and Zellkulturen GmbH (DSMZ), Mascheroder Weg 1B, 38124 Braunschweig, Deutschland, under the rules of the Budapest Treaty on 21.05.2005. The deposited microorganism has been given the accession number DSM 19369. Microorganism strain ST 108140 (DSM 19369) was classified as *Streptomyces* sp.

Instead of the strain *Streptomyces* sp. ST 108140 (DSM 19369), it is also possible to use its mutants and/or variants which synthesize one or more of the compounds according to the invention.

A mutant is a microorganism in which one or more genes in the genome has/have been modified, with the gene, or the genes, which is/are responsible for the ability of the organism to produce the compound according to the invention remaining functional and heritable.

Such mutants can be produced, in a manner known per se, using physical means, for example irradiation, as with ultraviolet rays or X-rays, or chemical mutagens, such as ethyl methanesulfonate (EMS); 2-hydroxy-4-methoxybenzophenone (MOB) or N-methyl-N'-nitro-N-nitrosoguanidine (MNNG), or as described by Brock et al. in "Biology of Microorganisms", Prentice Hall, pages 238-247 (1984).

A variant is a phenotype of the microorganism. Microorganisms have the ability to adapt to their environment and therefore exhibit highly developed physiological flexibility. All the cells of the microorganism are involved in the phenotypic adaptation, with the nature of the change not being genetically conditioned and being reversible under altered conditions (H. Stolp, Microbial ecology: organism, habitats, activities. Cambridge University Press, Cambridge, GB, page 180, 1988).

Screening for mutants and/or variants which synthesize one or more of the compounds according to the invention takes place in accordance with the following scheme:
1. lyophilizing the fermentation medium;
2. extracting the lyophilizate with an organic solvent
3. extracting the compound from the culture filtrate using solid phases
4. analyzing by means of HPLC or TLC or by testing the biological activity.

The fermentation conditions which have been described apply for *Streptomyces* sp. ST 108140 (DSM 19369) and for mutants and/or variants thereof.

A test which is based on determining the intracellular concentration of ATP is employed for measuring the bacterial viability. It relies on the fact that intact living bacteria have higher intra-cellular ATP levels than bacterial cells which are damaged by the action of antimicrobials. The formulation of the reagent supports bacterial cell lysis and ATP is quantified luminometrically by a luciferin/luciferase reaction.

The streptospirole derivatives of the formula (I) can be isolated and purified from the culture medium using known methods and taking account of the chemical, physical and biological properties of the natural substances. HPLC was used to test the concentrations of the respective streptospirole derivatives in the culture medium or in the individual isolation steps, with the quantity of the substance formed expediently being compared with a calibration solution.

For the isolation, the culture broth or the culture together with the solid medium is optionally lyophilized, after which the streptospirole derivatives are extracted from the lyophilizate using an organic solvent, for example methanol or 2-propanol. The organic solvent phase contains the natural substances of the formula (I) according to the invention; it is concentrated, where appropriate, under vacuum and subjected to further purification.

The further purification of one or more compounds of the formula (I) according to the invention is effected by chromatography on suitable materials, preferably, for example, on molecular sieves, on silica gel, on aluminum oxide, on ion exchangers or on adsorber resins or on reversed phases (RPs). This chromatography is used to separate the streptospirole derivatives. The streptospirole derivatives are chromatographed using buffered aqueous solutions or mixtures of aqueous and organic solutions.

Mixtures of aqueous or organic solutions are understood as being all water-miscible organic solvents, preferably methanol, 2-propanol or acetonitrile, at a concentration of from 5 to 95% solvent, preferably from 5 to 40% solvent, or else all buffered aqueous solutions which are miscible with organic solvents. The buffers which are to be used are the same as specified above.

The streptospirole derivatives are separated, on the basis of their differing polarities, by means of reversed phase chromatography, for example on polystyrene-divinylbenzene copolymer resin, MCI® (adsorber resin from Mitsubishi, Japan) or Amberlite XAD® (TOSOHAAS), or on other hydrophobic materials, for example on RP-8 or RP-18 phases. In addition, the separation can be effected by means of normal-phase chromatography, for example on silica gel, aluminum oxide and the like.

The streptospirole derivatives are chromatographed using buffered, basic or acidified aqueous solutions or mixtures of aqueous solutions with alcohols or other water-miscible organic solvents. Preference is given to using acetonitrile and methanol as organic solvent.

Buffered, basic or acidified aqueous solutions are understood as being, for example, water, phosphate buffer, ammonium acetate and citrate buffer at a concentration of up to 0.5 M, as well as formic acid, acetic acid, trifluoroacetic acid, ammonia and triethylamine, or all commercially available acids and bases known to the skilled person, preferably at a concentration of up to 1%. In the case of buffered aqueous solutions, particular preference is given to 0.1% ammonium acetate.

The chromatography is carried out using a gradient which begins with 100% water and ends with 100% solvent; the chromatography is preferably run with a linear gradient of from 5 to 95% acetonitrile.

Alternatively, it is also possible to carry out a gel chromatography or chromatography on hydrophobic phases. The gel chromatography is carried out on polyacrylamide gels or copolymer gels, such as Biogel-P 2® (Biorad) or Fractogel TSK HW 40® (Merck, Germany). The sequence of the above-mentioned chromatographic steps can be reversed.

Alkylation of the phenol OH group of a compound of the formula (I) wherein $R_2$ is H to a compound of the formula (I) wherein $R_2$ is $(C_1$-$C_6)$alkyl or $(C_1$-$C_6)$alkylene-OH, can be performed using methods which are known per se (J. March, Advanced Organic Chemistry, John Wiley & Sons, 4th edition, 1992). For example, methylation can be achieved by means of reaction with methyl iodide in the presence of a base. Derivatization by an ethylene-OH group can be achieved by reacting a compound of the formula (I) wherein $R_2$ is H with 2-(hydroxy)ethyl bromide in the presence of a base. Alternatively, the hydroxyl group in the substituent $(C_1$-$C_6)$alkylene-OH may be protected by the usual protecting groups and be deprotected after alkylation.

Nucleophilic substitution of a halogen atom, e.g. a chlorine atom as substituent $X_1$ to yield a compound of the formula (I) wherein $X_1$ is $O[(C_1$-$C_6)$alkyl] or $NH[(C_1$-$C_6)$alkyl], $NH[(C_1$-$C_4)$alkylene-$(C_6$-$C_{10})$-aryl], $NH[(C_1$-$C_4)$alkylene-$(C_6$-$C_{10})$-heteroaryl] or $S$—$(C_1$-$C_4)$alkylene-$N[(C_1$-$C_4)$alkyl]$_2$ is likewise effected using methods known per se, for example, reaction with isobutylamine, 4-picolylamine, 2-(diethylamino)ethanethiol hydrochloride in the presence of a base, or sodium $(C_1$-$C_6)$alkanolate, e.g. sodium methanolate, yields the respective $NH[(C_1$-$C_6)$alkyl], $NH[(C_1$-$C_4)$alkylene-$(C_6$-$C_{10})$-heteroaryl], $S$—$(C_1$-$C_4)$alkylene-$N[(C_1$-$C_4)$alkyl]$_2$ or $O[(C_1$-$C_6)$alkyl], substituents as $X_1$ (cf. Russian Journal of Organic Chemistry 2004, 40, 1521-1525; J. Heterocyclic Chem. 2002, 39, 203-211; Organic Letters 2004, 6 (9), 1481-1484).

Reduction of a benzofuran-3-one keto moiety in a compound of the formula (I) [$Y_1$ and $Y_2$ together are =O] to a 2,3-dihydro-benzofuran-3-ol [$Y_1$ and $Y_2$ are independently of each other H or OH] can be achieved by using methods known per se, for example, reaction with a borane derivative such as borane-tert-butylamine complex (JACS 1989, 111(1), 278-84; Eur. JOC 2006, 10, 2352-2361).

The conversion of a 2,3-dihydro-benzofuran-3-ol in a 2,3-dihydro-benzofuran-3-ylamine can be achieved by using methods known per se, for example, reaction with thionyl chloride (Bioorganic & Medicinal Chemistry Letters 2007, 17 (19), 5465-5471) followed by nucleophilic substitution of the chlorine by reaction with N-Methyl-piperazine or 4-fluoro-benzylamine (Journal of Medicinal Chemistry 2003, 46(4), 623-633).

The invention further relates to the use of a compound of the formula (I) or a physiologically tolerated salt thereof for use as a pharmaceutical in human or animal medicine, in particular for the treatment and/or prophylaxis of bacterial infections, preferably for the treatment and/or prophylaxis of bacterial infections related to Gram-positive pathogens such as for example Streptococci, Staphylococci and Enterococci.

A further embodiment of the present invention relates to a pharmaceutical composition having a content of at least one compound of the formula (I) or a physiologically tolerated salt thereof. Preferably, the pharmaceutical composition contains at least one compound of the formula (I) or a physiologically tolerated salt thereof and one or more of the customary, pharmacologically suitable carrier substances or auxiliary substances.

The compounds according to the invention are stable in the solid state and in solutions in a pH range of between 2 and 9, in particular 5 and 7, and, as a consequence, can be incorporated into the pharmaceutical composition.

While the pharmaceutical composition according to the invention can be administered orally or parenterally, a rectal use is also possible in principle. Examples of suitable solid or liquid pharmaceutical compositions are granules, powders, tablets, sugar-coated tablets, (micro)capsules, suppositories, syrups, emulsions, suspensions, aerosols, drops or injectable solutions in ampoule form, as well as preparations giving a protracted release of active compound, in connection with whose preparation use is customarily made of pharmacologically suitable carrier substances or auxiliary substances, such as disintegrants, binders, coating agents, swelling agents, glidants, lubricants, flavoring substances, sweeteners or solubilizers, for example magnesium carbonate, titanium dioxide, lactose, mannitol and other sugars, talc, milk protein, gelatin, starch, vitamins, cellulose and its derivatives, animal or vegetable oils, polyethylene glycols and solvents, such as sterile water, alcohols, glycerol and polyhydric alcohols.

Where appropriate, the dosage units for oral administration can be microencapsulated in order to delay release or to extend it over a relatively long period, for example by means of coating or embedding the active compound in particle form in suitable polymers, waxes or the like.

Preference is given to producing and administering the pharmaceutical preparations in dosage units, with each unit containing, as the active constituent, a defined dose of one or more compounds of the compound of the formula (I) or a physiologically tolerated salt thereof. In the case of solid dosage units such as tablets, capsules and suppositories, this dose can be up to about 500 mg, preferably, however, from about 0.1 to 200 mg, and, in the case of injection solutions in ampoule form, up to about 200 mg, preferably, however, from about 0.5 to 100 mg, per day.

The daily dose which is to be administered depends on the bodyweight, age, sex and condition of the mammalian subject. However, higher or lower daily doses may also possibly be appropriate. The daily dose can be administered both by means of once-only administration in the form of a single dosage unit, or else in several smaller dosage units, and by means of the multiple administration of subdivided doses at defined intervals.

The pharmaceuticals according to the invention are produced by bringing one or more of the compounds of the formula (I) into a suitable form for administration, optionally together with one or more of the customary carrier substances or auxiliary substances.

The compounds of the formula (I) are used in a test as further outlined in Examples section in a single dose of 0.125-64μg/ml and a dose dependency is given as a $IC_{50}$ value in Table 6.

The following examples are intended to explain the invention in more detail without limiting its scope in any way. Unless otherwise indicated, percentage values refer to the weight and mixing ratios in the case of liquids refer to the volume.

EXAMPLE 1

Storage of *Streptomyces* sp. ST 108140 (DSM 19369)

An agar plate (10.0 g/l malt extract, 4.0 g/l yeast extract, 4.0 g/l glucose, 15.0 g/l agar pH 7.0) was inoculated with the strain *Streptomyces* sp. ST 108140 (DSM 19369) and incubated at 28° C. for approx. 7 to 10 days. The cells were cut of the plate, re-suspended in 0.5 ml of 50% glycerol and stored at −135° C.

EXAMPLE 2

Preparing a Preliminary Culture of *Streptomyces* sp. ST 108140 (DSM 19369) in an Erlenmeyer Flask 100 ml of nutrient solution (4.0 g/l glucose, 4.0 g/l yeast extract, 10.0 g/malt extract, 2.0 g/l $CaCO_3$) in a sterile 300 ml Erlenmeyer flask was inoculated with the strain *Streptomyces* sp. ST 108140 (DSM 19369) and the culture was incubated for 7 days at 28° C. and 180 rpm on a rotating shaker. 10 ml of this preliminary culture were then used for preparing the main cultures.

EXAMPLE 3

Preparing a Liquid Main Culture of *Streptomyces* sp. ST 108140 (DSM 19369)

A sterile 300 ml Erlenmeyer flask containing 100 ml of the following nutrient solution (4.0 g/l yeast extract, 10.0 g/l malt extract, 4.0 g/l glucose, pH 7.0) was inoculated with 10 ml of a preliminary culture (see example 2), and incubated at 28° C. and 180 rpm on a shaker. The maximum production of the streptospiroles according to the invention was reached after 120-168 hours. A 96-120 hour-old submerged culture (inoculation quantity approx. 5-10%) from the same nutrient solution as described in Example 2 was sufficient for inoculating from 10 to 200 l fermenters.

EXAMPLE 4

Preparing Streptospirole Derivatives in a Fermenter

The 10 l and 30 l fermenters were operated under the following conditions:

| | | |
|---|---|---|
| Inoculum: | approx. 10% | approx. 10% |
| Fermenter: | 30 l | 10 l |
| Nutrient medium: | see example 2 | see example 2 |
| Incubation temperature: | 28° C. | 28° C. |
| Stirrer speed: | 112 rpm | 150 rpm |
| Aeration: | 8 l/min | 4 l/min |
| pH regulation: | from pH 7.8 to pH 7.5 | from pH 8.1 to pH 7.5 |
| $pO_2$ regulation: | none | none |

The pH was regulated using 10% KOH or, 10% $H_2SO_4$, respectively. Foam formation was suppressed by e.g. repeatedly adding Clerol FBA 265 (Cognis Deutschland GmbH). Maximum production is reached after approx. 72 to 96 hours.

EXAMPLE 5

Isolating Streptospirole Derivatives of the Formula (I) from the Shaken Cultures of *Streptomyces* sp. ST 108140 (DSM 19369)

After the *Streptomyces* sp. ST 108140 (DSM 19369) fermentation had come to an end, the culture broth from example 3 (30 l culture broth) was separated from the biomass by centrifugation. The biomass was extracted with a mixture of 90% methanol and 10% water (4×5 l). The methanol extract was reduced to 5 l under vacuum and then loaded together with the culture broth (30 l) onto a prepared column. The HPLC conditions are as follows:
Column: Mitsubishi Chemical Corporation—MCI® gel (130 mm×200 mm, packed with approx. 4 l of 75-150µ CHP-20P material)
Mobile phase:
Solution A=water with $NH_4OAc$ (50 g/l)=>pH=7.0
Solution B=isopropanol
Elution gradient: 40→100% B over 30 min, 100% B over 15 min
Flow rate: 240 ml/min
U.V. detection λ: 222 nm
Fraction volume: 1 l After analysis by HPLC, the fractions containing the streptospirole derivatives (fractions 6 to 8) were combined, reduced to a volume of 1.5 l under vacuum and lyophilized.
Analytical HPLC conditions are as follows:
Pre-column: Phenomenex (4 mm×2 mm, C18 ODS Octadecyl)
Column: Phenomenex—Luna® (2 mm×30 mm, 3µ C18 (2) 100 A)
Mobile phase:
Solution A=water with $NH_4OAc$ (50 g/l)=>pH=7.0
Solution B=acetonitrile
Elution gradient: 5→95% B over 6 min
Flow rate: 0.85 ml/min
U.V. detection λ: 220 nm

EXAMPLE 6

Purifying Streptospirole Derivatives (II), (III) and (IV) by means of RP-18 Chromatography The half (800 mg) of the lyophilizate obtained in Example 5 was purified by HPLC coupled with DAD-UV detection. The column conditions are as follows:
Pre-column: Waters—XTerra® (19 mm×10 mm, 10µ C18)
Column: Varian—Dynamax Pursuit® (40 mm×100 mm, 10µ C18)
Mobile phase:
Solution A=water with $NH_4OAc$ (50 g/l)=>pH=7.0
Solution B=acetonitrile
Elution gradient: 10→95% B over 30 min, 95% B over 5 min
Flow rate: 170 ml/min
U.V. detection λ: 222 nm
Fraction volume: 34 ml
Analysis by HPLC (same conditions as in Example 5) showed that the fractions 32-33 contain the compound of the formula (II), fractions 28-30 contain the compound of the formula (III) and fraction 36 contains the compound of the formula (IV).

The second half (800 mg) of the lyophilizate obtained in Example 5 was purified by HPLC coupled with DAD-UV detection. The column conditions are as follows:
Pre-column: Waters—XTerra® (19 mm×10 mm, 10µ C18)
Column: Varian—Dynamax Pursuit® (40 mm×100 mm, 10µ C18)
Mobile phase:
Solution A=water with $NH_4OAc$ (50 g/l)=>pH=7.0
Solution B=acetonitrile
Elution gradient: 20→95% B over 30 min, 95% B over 5 min
Flow rate: 120 ml/min
U.V. detection λ: 222 nm
Fraction volume: 24 ml
Analysis by HPLC (same conditions as in Example 5) showed that fraction 29 contains the compound of the formula (II), fractions 19-26 contain the compound of the formula (III) and fractions 33-35 contain the compound of the formula (IV).

After lyophilization, fractions 32+33 (column 1) added to fraction 29 (column 2) yielded 54.3 mg of compound (II) (purity>95%), fractions 28-30 (column 1) added to fractions 19-26 (column 2) yielded 44.9 mg of compound (III) (purity>95%) and fraction 36 (column 1) added to fractions 33-35 (column 2) yielded 67.3 mg of compound (IV) (purity>95%).

EXAMPLE 7

Isolating a Mixture of Streptospirole Derivatives of the Formula (I) from the Shaken Cultures of *Streptomyces* sp. ST 108140 (DSM 19369) fed with $CaBr_2$.

After the *Streptomyces* sp. ST 108140 (DSM 19369) fermentation including $CaBr_2$ had come to an end, the culture broth from example 3 (30 l culture broth) was separated from the biomass through centrifuge. The biomass was extracted with a mixture of 90% methanol and 10% water (4×5 l). The methanol extract was reduced to 5 l under vacuum and then loaded together with the culture broth (30 l) onto the same column as in Example 5, also with the same conditions.

After analysis by HPLC (same conditions as in Example 5), fractions (9 to 12) and the post-run fractions (1 and 2) containing the streptospirole derivatives were combined, reduced to a volume of 2.0 l under vacuum and lyophilized.

EXAMPLE 8

Purifying Mixture of Streptospirole Derivatives of the Formula (I) by Normal Phase and RP-18 Chromatography 2.0 g of the lyophilizate obtained in Example 7 was purified by silica gel chromatography. The column conditions are as follows:
Column: Separtis—Isolute® (Flash Si II, Silica Gel 60, 0.015-0.04 mm, sorbent mass: 70 g; reservoir volume: 150 mL)
Eluent: 1% methanol in dichloromethane
Fraction volume: 30 ml
After analysis by TLC (same eluent as used for the column) and evaporation under vacuum, fractions 9-17 yielded 186 mg of a mixture of the compounds of the formulae (II), (III), (IV), (VI), (VII), (VIII), (IX), (X), (XI), (XII), (XIII) and (XIV).

One third (62 mg) of the mass obtained in the precedent paragraph was purified by HPLC coupled with DAD-UV detection. The column conditions are as follows:
Pre-column: Waters—XTerra® (19 mm×10 mm, 10μ C18)
Column: Phenomenex—Luna® (30 mm×75 mm, 5μ C18 (2))
Mobile phase:
Solution A=water with $NH_4OAc$ (50 g/l) adjusted with ammonia=>pH=9.0
Solution B=acetonitrile
Elution gradient: 50→70% B over 44 min, 70→95% B over 1 min and 95% B over 5 min
Flow rate: 60 ml/min
U.V. detection λ: 220 nm
Fraction volume: 15 ml Analysis by HPLC (same conditions as in Example 5) shows that the fractions 1+2 contain a mixture of the compounds of the formulae (II), (III), (VI), (VII), (VIII), (IX), (X) and (XI), fractions 3+4 contain a mixture of the compounds of the formulae (IV), (XII), (XIII) and (XIV).

A second third (62 mg) of the mass obtained in Example 8 was purified by HPLC coupled with DAD-UV detection. The column conditions are as follows:
Pre-column: Waters—XTerra® (19 mm×10 mm, 10μ C18)
Column: Phenomenex—Luna® (30 mm×75 mm, 5μ C18 (2))
Mobile phase:
Solution A=water with $NH_4OAc$ (50 g/l) adjusted with ammonia=>pH=9.0
Solution B=acetonitrile
Elution gradient: 40→60% B over 44 min, 60→95% B over 1 min and 95% B over 5 min
Flow rate: 60 ml/min
U.V. detection λ: 220 nm
Fraction volume: 15 ml Analysis by HPLC (same conditions as in Example 5) showed that the fractions 1-3 contained a mixture of the compounds of the formulae (II), (III), (VI), (VII), (VIII), (IX), (X) and (XI), fractions 4+5 contained a mixture of the compounds of the formulae (IV), (XII), (XIII) and (XIV).

The last third (62 mg) of the mass obtained in Example 8 was purified by HPLC coupled with DAD-UV detection. The column conditions are as follows:
Pre-column: Waters—XTerra® (19 mm×10 mm, 10μ C18)
Column: Phenomenex—Luna® (30 mm×75 mm, 5μ C18 (2))
Mobile phase:
Solution A=water with $NH_4OAc$ (50 g/l) adjusted with ammonia=>pH=9.0
Solution B=acetonitrile
Elution gradient: 10→50% B over 44 min, 50→95% B over 1 min and 95% B over 5 min
Flow rate: 60 ml/min
U.V. detection λ: 220 nm
Fraction volume: 15 ml Analysis by HPLC (same conditions as in Example 5) showed that the fractions 1-6 contained a mixture of the compounds of the formulae (II), (III), (VI), (VII), (VIII), (IX), (X) and (XI), fractions 7-9 contained a mixture of the compounds of the formulae (IV), (XII), (XIII) and (XIV).

After lyophilization, fractions 1+2 (column 1), fractions 1-3 (column 2) and fractions 1-6 (column 3) yielded 3.1 mg of a mixture of the compounds of the formulae (II), (III), (VI), (VII), (VIII), (IX), (X) and (XI); fractions 3+4 (column 1), fractions 4+5 (column 2) and fractions 7-9 (column 3) yielded 4.4 mg of a mixture of the compounds of the formulae (IV), (XII), (XIII) and (XIV).

EXAMPLE 9

Preparing Streptospirole Derivative of the Formula (XVI)

Methyl iodide (7.8μL; 0.13 mmol; 5.0 equiv.) was added under argon to a solution of the compound of the formula (IV) (9.95 mg; 0.025 mmol; 1.0 equiv.) and $K_2CO_3$ (17.5 mg; 0.13 mmol; 5.0 equiv.) in dry DMF (1 mL). The reaction mixture was heated at 40° C. during 3 h.

EXAMPLE 10

Purifying the Streptospirole Derivative of the Formula (XVI)

After filtration of the reaction mixture obtained in Example 9, the solvent was removed by lyophilisation and the desired product isolated quantitatively (9.8 mg).

EXAMPLE 11

Preparing Streptospirole Derivative of the Formula (XVII)

Isobutylamine (30.0μL; 0.3 mmol; 10.0 equiv.) was added under argon to a solution of the compound of the formula (II) (11.52 mg; 0.03 mmol; 1.0 equiv.) and triethylamine (27.0μL; 0.3 mmol; 10.0 equiv.) in dry $CH_2Cl_2$ (1 mL). The reaction mixture was heated at 50° C. during 12 h.

EXAMPLE 12

Purifying the Streptospirole Derivative of the Formula (XVII)

The crude extract (44 mg) obtained after removing under vacuum the solvent from example 11 was purified by silica gel chromatography. The column conditions are as follows:
Column: Separtis—Isolute® (Flash Si II, Silica Gel 60, 0.015-0.04 mm, sorbent mass: 5 g; reservoir volume: 25 mL)
Eluent: 40% ethyl acetate in heptane
Fraction volume: 5 ml After analysis by TLC (same eluent as used for the column) and evaporation under vacuum, fractions 9-14 yielded 7.7 mg (61%) of the desired compound (XVII).

EXAMPLE 13

Preparing Streptospirole Derivative of the Formula (XVIII)

4-picolyl-amine (28.0μL; 0.3 mmol; 10.0 equiv.) was added under argon to a solution of the compound of the formula (II) (11.52 mg; 0.03 mmol; 1.0 equiv.) and triethylamine (27.0μL; 0.3 mmol; 10.0 equiv.) in dry $CH_2Cl_2$ (1 mL). The reaction mixture was heated at 50° C. during 12 h.

EXAMPLE 14

Purifying the Streptospirole Derivative of the Formula (XVIII)

The crude extract (56 mg) obtained after removing under vacuum the solvent from example 13 is purified by HPLC coupled with DAD-UV detection. The column conditions are as follows:
Pre-column: Waters—XTerra® (19 mm×10 mm, 10μ C18)
Column: Phenomenex—Luna® (30 mm×75 mm, 5μ C18 (2))
Mobile phase:
Solution A=water with 10% trifluoroacetic acid=>pH=1.0
Solution B=acetonitrile
Elution gradient: 5→95% B over 45 min, 95% B over 5 min
Flow rate: 60 ml/min
U.V. detection λ: 212 nm
Fraction volume: 15 ml
After analysis by HPLC (same conditions as in Example 5) and lyophilization, the fractions 18-22 yielded 9.9 mg (73%) of the desired compound.

EXAMPLE 15

Preparing Streptospirole Derivative of the Formula (XIX)

2-(Diethylamino)ethanethiol hydrochloride (85.0 mg; 0.5 mmol; 10.0 equiv.) was added under argon to a solution of the compound of the formula (II) (19.2 mg; 0.05 mmol; 1.0 equiv.) and sodium hydride (12.0 mg; 0.5 mmol; 10.0 equiv.) in dry $CH_2Cl_2$ (2 mL). The reaction mixture was heated at 50° C. during 3 h.

EXAMPLE 16

Purifying the Streptospirole Derivative of the Formula (XIX)

The crude extract (74 mg) obtained after removing under vacuum the solvent from example 15 was purified by HPLC coupled with DAD-UV detection. The column conditions are as follows:
Pre-column: Waters—XTerra® (19 mm×10 mm, 10μ C18)
Column: Phenomenex—Luna® (30 mm×75 mm, 5μ C18 (2))
Mobile phase:
Solution A=water with $NH_4OAc$ (50 g/l)=>pH=7.0
Solution B=acetonitrile
Elution gradient: 5→95% B over 45 min, 95% B over 5 min
Flow rate: 60 ml/min
U.V. detection λ: 220 nm
Fraction volume: 15 ml
After analysis by HPLC (same conditions as in Example 5) and lyophilization, the fractions 7-12 yielded 10.4 mg (43%) of the desired compound (XIX).

EXAMPLE 17

Preparing Streptospirole Derivative of the Formula (XX)

2-(Hydroxy)ethyl bromide (9.40μL; 0.13 mmol; 5.0 equiv.) was added under argon to a solution of the compound of the formula (III) (9.98 mg; 0.026 mmol; 1.0 equiv.) and $K_2CO_3$ (18.2 mg; 0.13 mmol; 5.0 equiv.) in dry DMF (1 mL). The reaction mixture was heated at 70° C. during 3 h.

EXAMPLE 18

Purifying the Streptospirole Derivative of the Formula (XX)

The crude extract (52 mg) obtained after filtration and removing under vacuum the solvent from example 17 was purified by silica gel chromatography. The column conditions are as follows:
Column: Separtis—Isolute® (Flash Si II, Silica Gel 60, 0.015-0.04 mm, sorbent mass: 5 g; reservoir volume: 25 mL)
Eluent: 2% methanol in dichloromethane
Fraction volume: 5 ml
After analysis by TLC (same eluent as used for the column) and evaporation under vacuum, fractions 2-3 yielded 6.7 mg (60%) of the desired compound.

EXAMPLE 19

Preparing Streptospirole Derivatives of the Formula (XXI)

Boran-t-butylamin complex (43.5 mg; 0.5 mmol; 5.0 equiv.) was added to a solution of a compound of the formula (IV) (39.80 mg; 0.1 mmol; 1.0 equiv.) in a mixture of THF/AcOH 9/1. The reaction mixture was heated at 55° C. during 3 h.

EXAMPLE 20

Purifying the Streptospirole Derivatives of the Formulae (XXI)

The crude extract (89 mg) obtained after removing under vacuum the solvents from example 19 was purified by HPLC coupled with DAD-UV detection. The column conditions are as follows:
Pre-column: Waters—XTerra® (19 mm×10 mm, 10μ C18)
Column: Phenomenex—Luna® (30 mm×75 mm, 5μ C18 (2))
Mobile phase:
Solution A=water with $NH_4OAc$ (50 g/l)=>pH=7.0
Solution B=acetonitrile
Elution gradient: 5→95% B over 45 min, 95% B over 5 min
Flow rate: 60 ml/min
U.V. detection λ: 220 nm
Fraction volume: 15 ml
After analysis by HPLC (same conditions as in Example 5) and lyophilization, the fractions 1-3 yielded 4.6 mg (12%) of one stereoisomer and the fractions 4-7 yielded 10.0 mg (25%) of another stereoisomer of compound (XXI) [(1S,8R,16S)-(XXI) and (1R,8R,16S)-(XXI)].

EXAMPLE 21

Preparing Streptospirole Derivatives of the Formulae (XXII a and XXII b)

Boran-t-butylamin complex (33.7 mg; 0.39 mmol; 3.0 equiv.) was added to a solution of a compound of the formula (II) (49.6 mg; 0.13 mmol; 1.0 equiv.) in a mixture of THF/AcOH 9/1 (3.0 mL). The reaction mixture was heated at 60° C. during 3 h.

The crude extract (59 mg) obtained after removing under vacuum the solvents was purified by silica gel chromatography. The column conditions are as follows:
Column: Separtis—Isolute® (Flash Si II, Silica Gel 60, 0.015-0.04 mm, sorbent mass: 5 g; reservoir volume: 25 mL)
Eluent: 3% methanol in dichloromethane
Fraction volume: 5 ml After analysis by TLC (same eluent as used for the column) and evaporation under vacuum, fractions 2-5 yielded 32.3 mg (65%) of the mixture of the 2,3-dihydro-benzofuran-3-ol diastereoisomers.

Thionyl chloride (33.0µL; 0.81 mmol; 10.0 equiv.) was added to a solution of the mixture of the 2,3-dihydro-benzofuran-3-ol intermediates (32.3 mg; 0.08 mmol; 1.0 equiv.) in dry $CH_2Cl_2$ (1.5 mL). The reaction mixture was heated at 60° C. during 3 h.

The crude extract obtained after removing under vacuum the dichloromethane was dissolved in acetonitrile (3.0 mL) and slowly added by isobutylamin (11.7µL; 0.40 mmol; 5.0 equiv.). The reaction mixture was leaved at room temperature during 1 h.

EXAMPLE 22

Purifying the Streptospirole Derivatives of the Formulae (XXIIa and XXIIb)

The crude extract (61 mg) obtained after removing under vacuum the solvent from example b was purified by HPLC coupled with DAD-UV detection. The column conditions are as follows:
Pre-column: Waters—XTerra® (19 mm×10 mm, 10µ C18)
Column: Phenomenex—Luna® (30 mm×75 mm, 5µ C18 (2))
Mobile phase:
Solution A=water with $NH_4OAc$ adjusted with acetic acid=>pH=4.6
Solution B=acetonitrile
Elution gradient: 40→95% B over 45 min, 95% B over 5 min
Flow rate: 60 ml/min
U.V. detection λ: 220 nm
Fraction volume: 15 ml After analysis by HPLC (same conditions as in Example 5) and lyophilization, the fractions 7-10 yielded 7.7 mg (13% overall yield) of the compound (XXIIa) and the fractions 12-14 yielded 2.3 mg (4% overall yield) of the compound (XXIIb).

EXAMPLE 23

Preparing Streptospirole Derivatives of the Formulae (XXIII and XXIV)

Boran-t-butylamin complex (68.0 mg; 0.78 mmol; 3.0 equiv.) was added to a solution of a compound of the formula (III) (99.6 mg; 0.26 mmol; 1.0 equiv.) in a mixture of THF/AcOH 9/1 (5.0 mL). The reaction mixture was heated at 60° C. during 4 h.

The crude extract (135 mg) obtained after removing under vacuum the solvents was purified by silica gel chromatography. The column conditions are as follows:
Column: Separtis—Isolute® (Flash Si II, Silica Gel 60, 0.015-0.04 mm, sorbent mass: 10 g; reservoir volume: 70 mL)
Eluent: 3% methanol in dichloromethane
Fraction volume: 5 ml After analysis by TLC (same eluent as used for the column) and evaporation under vacuum, fractions 3-9 yielded 66.9 mg (67%) of the mixture of the 2,3-dihydro-benzofuran-3-ol diastereoisomers.

Thionyl chloride (66.0µL; 1.62 mmol; 10.0 equiv.) was added to a solution of the mixture of the 2,3-dihydro-benzofuran-3-ol intermediates (66.9 mg; 0.17 mmol; 1.0 equiv.) in dry $CH_2Cl_2$ (3.0 mL). The reaction mixture was heated at 60° C. during 3 h.

The half of the crude extract obtained after removing under vacuum the dichloromethane was dissolved in acetonitrile (2.0 mL) and slowly added by N-Methyl-piperazine (53.0µL; 0.43 mmol; 5.0 equiv.). The reaction mixture was leaved at room temperature during 1 h.

The other half of the crude extract obtained after removing under vacuum the dichloromethane was dissolved in acetonitrile (2.0 mL) and slowly added by 4-fluoro-benzylamine (66.0µL; 0.43 mmol; 5.0 equiv.). The reaction mixture was leaved at room temperature during 1 h.

EXAMPLE 24

Purifying the Streptospirole Derivative of the Formula (XXIII)

The crude extract (70 mg) obtained after removing under vacuum the solvent from example d was purified by HPLC coupled with DAD-UV detection. The column conditions are as follows:
Pre-column: Waters—XTerra® (19 mm×10 mm, 10µ C18)
Column: Phenomenex—Luna® (30 mm×75 mm, 5µ C18 (2))
Mobile phase:
Solution A=water with $NH_4OAc$ adjusted with acetic acid=>pH=4.6
Solution B=acetonitrile
Elution gradient: 40→95% B over 45 min, 95% B over 5 min
Flow rate: 60 ml/min
U.V. detection λ: 220 nm
Fraction volume: 15 ml After analysis by HPLC (same conditions as in Example 5) and lyophilization, the fractions 20-24 yielded 11.9 mg (19% overall yield) of the compound (XXIII).

EXAMPLE 25

Purifying the Streptospirole Derivative of the Formula (XXIV)

The crude extract (61 mg) obtained after removing under vacuum the solvent from example d was purified by HPLC coupled with DAD-UV detection. The column conditions are as follows:

Pre-column: Waters—XTerra® (19 mm×10 mm, 10μ C18)

Column: Phenomenex—Luna® (30 mm×75 mm, 5μ C18 (2))

Mobile phase:

Solution A=water with NH₄OAc adjusted with acetic acid=>pH=4.6

Solution B=acetonitrile

Elution gradient: 30=95% B over 45 min, 95% B over 5 min

Flow rate: 60 ml/min

U.V. detection λ: 220 nm

Fraction volume: 15 ml

After analysis by HPLC (same conditions as in Example 5) and lyophilization, the fractions 10-12 yielded 9.6 mg (16% overall yield) of the compound (XXIV).

EXAMPLE 26

Preparing Streptospirole Derivative of the Formula (XXV)

Sodium methanolate (54.0 mg; 1.0 mmol; 10.0 equiv.) was added under argon to a solution of the compound of the formula (IV) (39.8 mg; 0.1 mmol; 1.0 equiv.) in dry methanol (2.0 mL). The reaction mixture was heated at 80° C. during 12 h.

EXAMPLE 27

Purifying the Streptospirole Derivative of the Formula (XXV)

The crude extract (101 mg) obtained after removing under vacuum the solvent from example g was purified by silica gel chromatography. The column conditions are as follows:

Column: Separtis—Isolute® (Flash Si II, Silica Gel 60, 0.015-0.04 mm, sorbent mass: 10 g; reservoir volume: 70 mL)

Eluent: 2% methanol in dichloromethane

Fraction volume: 5 ml

After analysis by TLC (same eluent as used for the column) and evaporation under vacuum, fractions 8-15 yielded 10.2 mg (26%) of the compound (XXV).

EXAMPLE 28

Characterizing the Compound of the Formula (R)-(II), Streptospirole A

ESI-MS (neg): [M−H]⁻=382.0633

Experimental neutral monoisotopic mass Exact, [M]=383.07058

Neutral monoisotopic mass calculated for $C_{18}H_{19}Cl_2NO_4$: 383.06911

Molecular formula: $C_{18}H_{19}Cl_2NO_4$

Chemical molecular weight=384.26

$[\alpha]_D^{20}$=+52.7 (c=0.75 g/100 mL, CH₃OH)

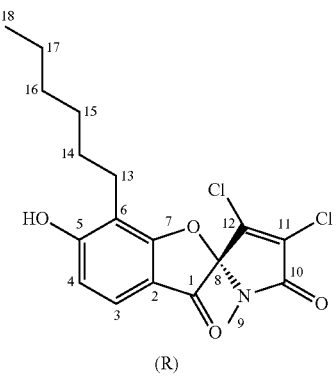

(II)

(R)

The NMR data of streptospirole A (II) are listed in Table 1. The data have been acquired on an AVANCE 600 instrument from Bruker operating at 600 MHz (¹H) and 150 MHz (¹³C). All spectra have been recorded in DMDS-d6 at 303K. The structure elucidation is based on the analyses of various 2D-NMR experiments including DQF-COSY, HSQC, and HMBC.

TABLE 1

Chemical shifts of Streptospirole A (II) at 303 K in DMSO-d6.

| | ¹H | ¹³C |
|---|---|---|
| 1 | — | 187.0 |
| 2 | — | 109.2 |
| 3 | 7.48 | 124.3 |
| 4 | 6.72 | 113.6 |
| 5 | — | 171.4 |
| 5-OH | 11.67 | — |
| 6 | — | 112.6 |
| 7 | — | 168.3 |
| 8 | — | 96.4 |
| 9 | 2.67 | 25.4 |
| 10 | — | 162.0 |
| 11 | — | 127.5 |
| 12 | — | 138.9 |
| 13 | 2.57 | 21.7 |
| 14 | 1.51 | 27.9 |
| 15 | 1.25/1.30 | 28.3 |
| 16 | 1.25 | 31.10 |
| 17 | 1.24 | 21.9 |
| 18 | 0.82 | 13.8 |

EXAMPLE 29

Characterizing the Compound of the Formula (R)-(III), Streptospirole B

ESI-MS (neg): [M−H]⁻=382.0623

Experimental neutral monoisotopic mass Exact, [M]=383.06958

Neutral monoisotopic mass calculated for $C_{18}H_{19}Cl_2NO_4$: 383.06911

25

Molecular formula: $C_{18}H_{19}Cl_2NO_4$
Chemical molecular weight=384.26
$[\alpha]_D^{20}$=+69.2 (c=0.70 g/100 mL, $CH_3OH$)

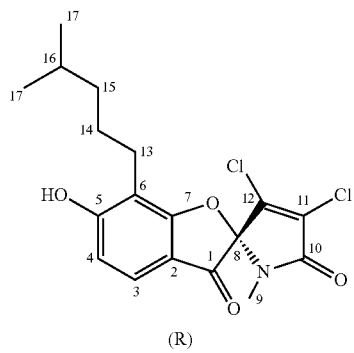

(III)

(R)

The NMR data of streptospirole B (III) are listed in Table 2. The experimental conditions are identical to those given in Example 28.

TABLE 2

Chemical shifts of Streptospirole B (III) at 303 K in DMSO-d6.

| | $^1H$ | $^{13}C$ |
|---|---|---|
| 1 | — | 185.8 |
| 2 | — | 107.9 |
| 3 | 7.41 | 124.1 |
| 4 | 6.60 | 114.6 |
| 5 | — | 170.3 |
| 5-OH | 11.85 | — |
| 6 | — | 112.2 |
| 7 | — | 171.2 |
| 8 | — | 96.5 |
| 9 | 2.66 | 25.4 |
| 10 | — | 162.0 |
| 11 | — | 127.2 |
| 12 | — | 139.3 |
| 13 | 2.57 | 21.9 |
| 14 | 1.47/1.52 | 25.9 |
| 15 | 1.17 | 38.1 |
| 16 | 1.49 | 27.2 |
| 17 | 0.81 | 22.4 |

EXAMPLE 30

Characterizing the Compound of the Formula (8R,16S)-(IV), Streptospirole C

ESI-MS (neg): $[M-H]^-$=396.0767
Experimental neutral monoisotopic mass Exact, [M]=397.08398
Neutral monoisotopic mass calculated for $C_{19}H_{21}Cl_2NO_4$: 397.08476
Molecular formula: $C_{19}H_{21}Cl_2NO_4$

26

Chemical molecular weight=398.29
$[\alpha]_D^{20}$=+66.3 (c=0.86 g/100 mL, $CH_3OH$)

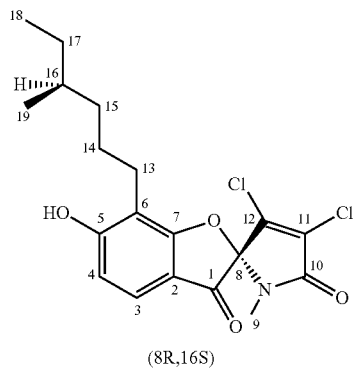

(IV)

(8R,16S)

The NMR data of streptospirole C (IV) are listed in Table 3. The experimental conditions are identical to those given in Example 28.

TABLE 3

Chemical shifts of Streptospirole C (IV) in DMSO at 303 K.

| | $^1H$ | $^{13}C$ |
|---|---|---|
| 1 | — | 186.9 |
| 2 | — | 109.2 |
| 3 | 7.49 | 124.2 |
| 4 | 6.73 | 113.6 |
| 5 | — | 171.3 |
| 5-OH | ~11.7 (broad) | — |
| 6 | — | 112.6 |
| 7 | — | 168.2 |
| 8 | — | 97.4 |
| 9 | 2.68 | 25.4 |
| 10 | — | 162.1 |
| 11 | — | 127.5 |
| 12 | — | 138.9 |
| 13 | 2.57 | 22.0 |
| 14 | 1.52 | 25.5 |
| 15 | 1.29/1.11 | 35.5 |
| 16 | 1.31 | 33.5 |
| 17 | 1.26/1.06 | 28.8 |
| 18 | 0.79 | 11.1 |
| 19 | 0.81 | 18.9 |

EXAMPLE 31

Characterizing the Compound of the Formula (8R,16S)-(XVI)

ESI-MS (pos, low resolution): $[M+H]^+$=412.2
Experimental neutral monoisotopic mass Exact, [M]=411.2
Neutral monoisotopic low resolution mass calculated for $C_{20}H_{23}Cl_2NO_4$: 411.1

Molecular formula: $C_{20}H_{23}Cl_2NO_4$
Chemical molecular weight=412.31

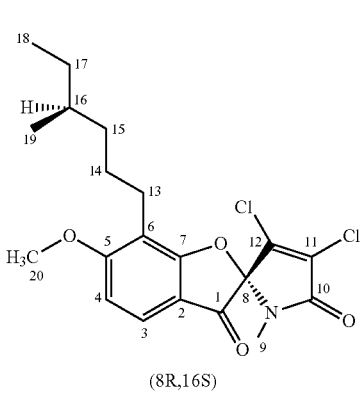

(8R,16S)

EXAMPLE 32

Characterizing the Compound of the Formula (R)-(XVII)

ESI-MS (neg): [M−H]⁻=419.1666
Experimental neutral monoisotopic mass Exact, [M]=420.17388
Neutral monoisotopic mass calculated for $C_{22}H_{29}ClN_2O_4$: 420.18159
Molecular formula: $C_{22}H_{29}ClN_2O_4$
Chemical molecular weight=420.94

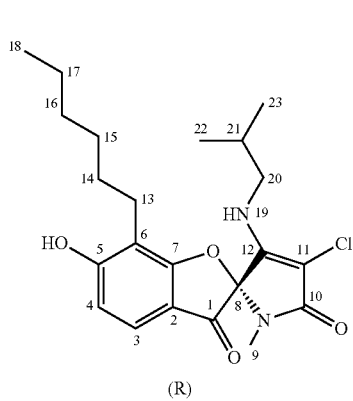

(R)

EXAMPLE 33

Characterizing the Compound of the Formula (R)-(XVIII)

ESI-MS (neg): [M−H]⁻=454.1582
Experimental neutral monoisotopic mass Exact, [M]=455.16548

Neutral monoisotopic mass calculated for $C_{24}H_{26}ClN_3O_4$: 455.16118
Chemical molecular weight=455.94

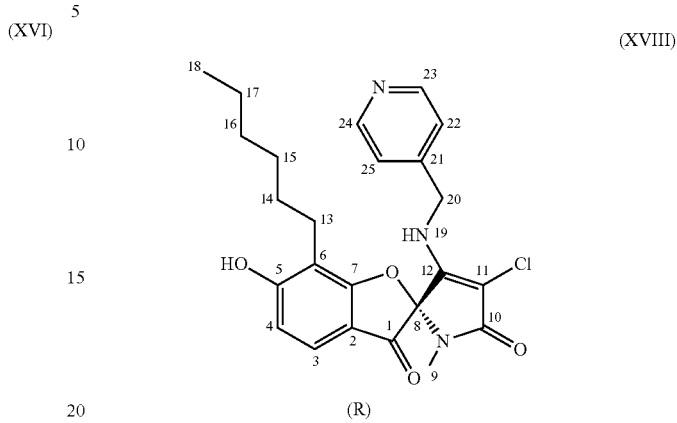

(R)

EXAMPLE 34

Characterizing the Compound of the Formula (R)-(XIX)

ESI-MS (neg): [M−H]⁻=479.1685
Experimental neutral monoisotopic mass Exact, [M]=480.17578
Neutral monoisotopic mass calculated for $C_{24}H_{33}ClN_2O_4S$: 480.18496
Molecular formula: $C_{24}H_{33}ClN_2O_4S$
Chemical molecular weight=481.06

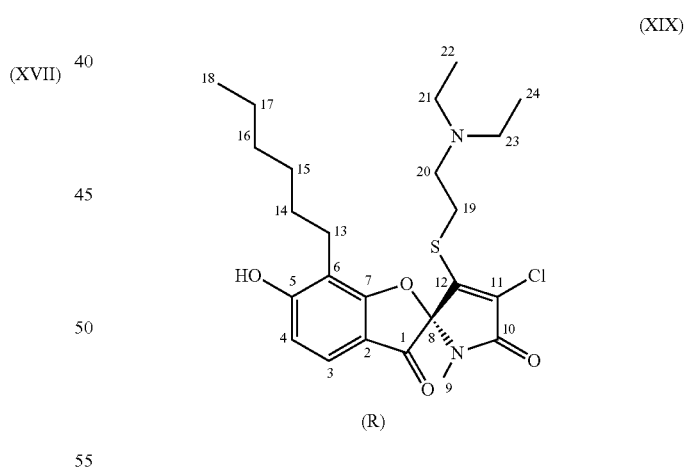

(R)

EXAMPLE 35

Characterizing the Compound of the Formula (R)-(XX)

ESI-MS (neg): [M+Acetate]⁻=486.1138
Experimental neutral monoisotopic mass Exact, [M]=427.09995
Neutral monoisotopic mass calculated for $C_{20}H_{23}Cl_2NO_5$: 427.09533

Molecular formula: C₂₀H₂₃Cl₂NO₅
Chemical molecular weight=428.31

Molecular formula: C₁₉H₂₃Cl₂NO₄
Chemical molecular weight=400.3

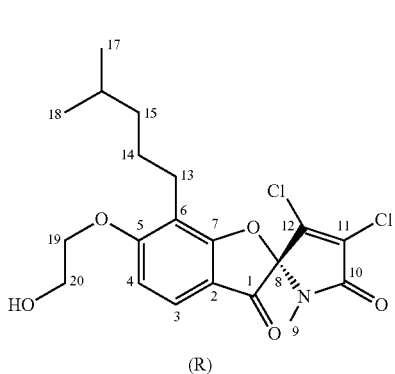

(XX)
(R)

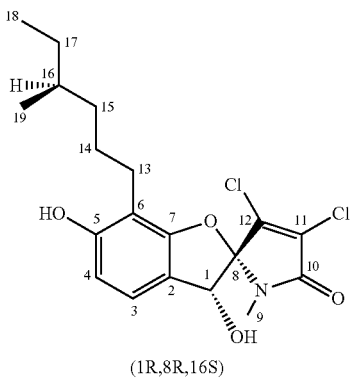

(XXI)
(1R,8R,16S)

EXAMPLE 36

Characterizing the Compound of the Formula (1S,8R,16S)-(XXI)

ESI-MS (neg): [M−H]⁻=398.0950
Experimental neutral monoisotopic mass Exact, [M]=399.10228
Neutral monoisotopic mass calculated for C₁₉H₂₃Cl₂NO₄: 399.10041
Molecular formula: C₁₉H₂₃Cl₂NO₄
Chemical molecular weight=400.3

EXAMPLE 38

Characterizing the Compound of the Formula (1S,8R)-(XXII a)

ESI-MS (neg): [M−H]⁻=439.1599
Experimental neutral monoisotopic mass Exact, [M]=440.16718
Neutral monoisotopic mass calculated for C₂₂H₃₀Cl₂N₂O₃: 440.16335
Molecular formula: C₂₂H₃₀Cl₂N₂O₃
Chemical molecular weight=441.4

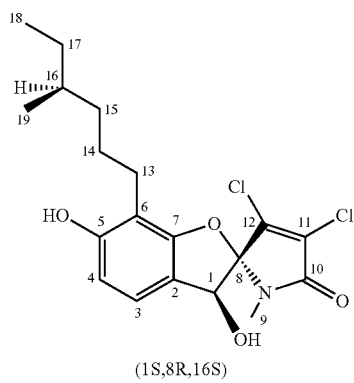

(XXI)
(1S,8R,16S)

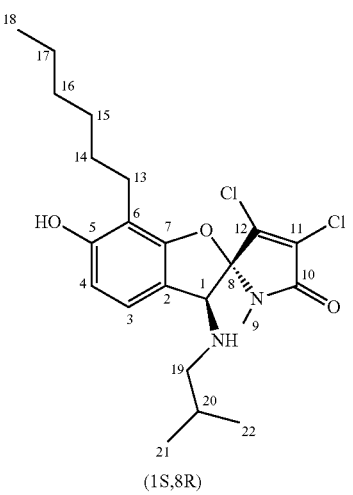

(XXIIa)
(1S,8R)

EXAMPLE 37

Characterizing the Compound of the Formula (1R,8R,16S)-(XXI)

ESI-MS (neg): [M−H]⁻=398.0950
Experimental neutral monoisotopic mass Exact, [M]=399.10228
Neutral monoisotopic mass calculated for C₁₉H₂₃Cl₂NO₄: 399.10041

EXAMPLE 39

Characterizing the Compound of the Formula (1R,8R)-(XXII b)

ESI-MS (neg): [M−H]⁻=439.1599
Experimental neutral monoisotopic mass Exact, [M]=440.16718
Neutral monoisotopic mass calculated for C₂₂H₃₀Cl₂N₂O₃: 440.16335

Molecular formula: $C_{22}H_{30}Cl_2N_2O_3$
Chemical molecular weight=441.4

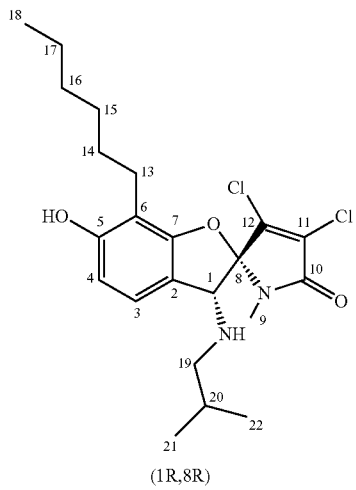

(XXIIb)

(1R,8R)

EXAMPLE 40

Characterizing the Compound of the Formula (1S,8R)-(XXIII)

ESI-MS (neg): $[M-H]^- = 491.1294$
Experimental neutral monoisotopic mass Exact, [M]=492.13668
Neutral monoisotopic mass calculated for $C_{25}H_{27}Cl_2FN_2O_3$: 492.13828
Molecular formula: $C_{25}H_{27}Cl_2FN_2O_3$
Chemical molecular weight=493.41

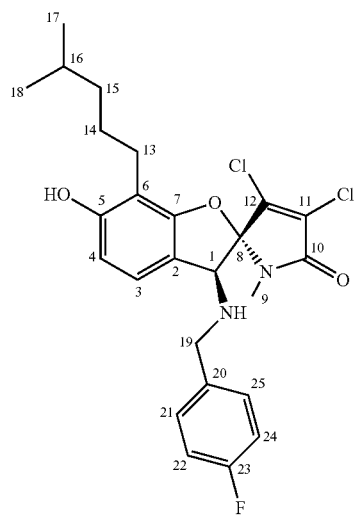

(XXIII)

(1S,8R)

EXAMPLE 41

Characterizing the Compound of the Formula (1S,8R)-(XXIV)

ESI-MS (neg): $[M-H]^- = 466.1653$
Experimental neutral monoisotopic mass Exact, [M]=467.17258
Neutral monoisotopic mass calculated for $C_{23}H_{31}Cl_2N_3O_3$: 467.17425
Molecular formula: $C_{23}H_{31}Cl_2N_3O_3$
Chemical molecular weight=468.43

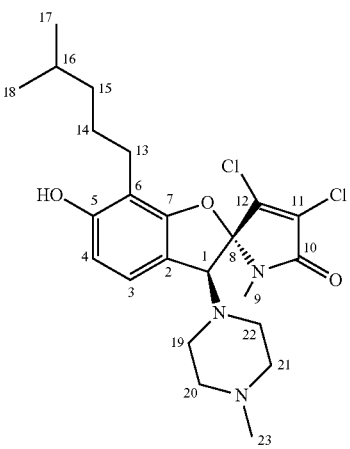

(XXIV)

(1S,8R)

EXAMPLE 42

Characterizing the Compound of the Formula (8R,16S)-(XXV)

ESI-MS (neg): $[M-H]^- = 392.1306$
Experimental neutral monoisotopic mass Exact, [M]=393.13788
Neutral monoisotopic mass calculated for $C_{20}H_{24}ClNO_5$: 393.1343
Molecular formula: $C_{20}H_{24}ClNO_5$
Chemical molecular weight=393.87

(XXV)

(8R,16S)

EXAMPLE 43

Characterization the Mixture of the Compounds of the Formulae (R)-(II), (R)-(III), (R)-(VI), (R)-(VII), (R)-(VIII), (R)-(IX), (R)-(X) and (R)-(XI) (Mix 1) as isolated in Example 7

Compounds (R)-(II) and (R)-(III):
ESI-MS (neg): [M−H]$^-$=382.0638
Experimental neutral monoisotopic mass Exact, [M]=383.07108
Neutral monoisotopic mass calculated for $C_{18}H_{19}Cl_2NO_4$: 383.06911
Molecular formula: $C_{15}H_{19}Cl_2NO_4$
Chemical molecular weight=384.26
cf. formulae in Examples 28 and 29

Compounds (R)-(VI), (R)-(VIII), (R)-(IX) and (R)-(XI):
ESI-MS (neg): [M−H]$^-$=426.0120
Experimental neutral monoisotopic mass Exact, [M]=427.01928
Neutral monoisotopic mass calculated for $C_{18}H_{19}BrClNO_4$: 427.0186
Molecular formula: $C_{18}H_{19}BrClNO_4$
Chemical molecular weight=428.71

Compounds (R)-(VII) and (R)-(X):
ESI-MS (neg): [M−H]$^-$=469.9616
Experimental neutral monoisotopic mass Exact, [M]=470.96888
Neutral monoisotopic mass calculated for $C_{18}H_{19}Br_2NO_4$: 470.96808
Molecular formula: $C_{18}H_{19}Br_2NO_4$
Chemical molecular weight=473.16

Determination of the products was done on a Waters Acquity UPLC-System with ELS and PDA-2996-Detector and a Bruker microTOF-LC mass-spectrometer. Data were collected with microTOF control 1.1 and MassLynx v 4.1 software. Chromatographic separation was done over an Acquity UPLC BEH-column (C18, 1.7μm; 2.1×100 mm) using a gradient of 90% A to 100% B within 15 min (A: water/Acetonitrile/buffer=90:5:5; B: water/Acetonitrile/buffer=5:95:5; buffer=6.5 mM ammonium acetate, pH 4.5). All data were subjected to Waters/Q-DIS Marlin software and gradients were extended to 30 min by correction-trait algorithm to match the database. The peaks and relative amounts of the respective compounds in Mix 1 are as follows:

| Peak [min] | Molecular formula | Chemical molecular weight | Compound [(R) each] | Relative amount [%] |
|---|---|---|---|---|
| 17.54 | $C_{18}H_{19}BrClNO_4$ | 428.71 | (VI), (VIII), (IX) or (XI) | 6.4 |
|  | $C_{18}H_{19}Br_2NO_4$ | 473.16 | (VII) or (X) | 8.0 |
| 17.68 | $C_{18}H_{19}Cl_2NO_4$ | 384.26 | (III) | 8.0 |
|  | $C_{18}H_{19}BrClNO_4$ | 428.71 | (VI), (VIII), (IX) or (XI) | 6.4 |
| 17.83 | $C_{18}H_{19}BrClNO_4$ | 428.71 | (VI), (VIII), (IX) or (XI) | 20.2 |
|  | $C_{18}H_{19}Br_2NO_4$ | 473.16 | (VII) or (X) | 12.1 |
| 17.96 | $C_{18}H_{19}Cl_2NO_4$ | 384.26 | (II) | 25.9 |
|  | $C_{18}H_{19}BrClNO_4$ | 428.71 | (VI), (VIII), (IX) or (XI) | 13.0 |

All peaks have the same streptospirole-like UV-spectrum with maxima of 211, 236 and 302 nm.

EXAMPLE 44

Characterizing the Mixture of the Compounds of the Formulae (8R,16S)-(IV), (8R,16S)-(XII), (8R,16S)-(XIII) and (8R,16S)-(XIV) (Mix 2) as Isolated in Example 7

Compound (8R,16S)-(IV):
ESI-MS (neg): [M−H]$^-$=396.0834
Experimental neutral monoisotopic mass Exact, [M]=397.09068
Neutral monoisotopic mass calculated for $C_{19}H_{21}Cl_2NO_4$: 397.08476
Molecular formula: $C_{19}H_{21}Cl_2NO_4$
Chemical molecular weight=398.29
cf. formula in Example 30

Compounds (8R,16S)-(XII) and (8R,16S)-(XIV):
ESI-MS (neg): [M−H]$^-$=440.0331
Experimental neutral monoisotopic mass Exact, [M]=441.04038
Neutral monoisotopic mass calculated for $C_{19}H_{21}BrClNO_4$: 441.03425
Molecular formula: $C_{19}H_{21}BrClNO_4$
Chemical molecular weight=442.74

Compound (8R,16S)-(XIII):
ESI-MS (neg): [M−H]$^-$=483.9798
Experimental neutral monoisotopic mass Exact, [M]=484.98708
Neutral monoisotopic mass calculated for $C_{19}H_{21}Br_2NO_4$: 484.98373
Molecular formula: $C_{19}H_{21}Br_2NO_4$
Chemical molecular weight=487.19

Determination of the products was performed as described in Example 43. The peaks and relative amounts of the respective compounds in Mix 2 are as follows:

| Peak [min] | Molecular formula | Chemical molecular weight | Compound [(8R,16S) each] | Relative amount [%] |
|---|---|---|---|---|
| 18.60 | $C_{19}H_{21}BrClNO_4$ | 442.74 | (XII) or (XIV) | 26.5 |
|  | $C_{19}H_{21}Br_2NO_4$ | 487.19 | (XIII) | 13.3 |
| 18.74 | $C_{19}H_{21}Cl_2NO_4$ | 398.29 | (IV) | 40.1 |
|  | $C_{19}H_{21}BrClNO_4$ | 442.74 | (XII) or (XIV) | 20.1 |

All peaks have the same streptospirole-like UV-spectrum with maxima of 211, 236 and 302 nm.

EXAMPLE 45

Determination of $IC_{50}$ Values by Broth Dilution Method-Microdilution

This Example describes the standard broth dilution method-microdilution used to determine the in vitro susceptibility of bacteria growing aerobically according to NCCLS M7-A7. The $IC_{50}$ value of the compound to be tested is calculated as the inhibitory concentration of 50% at which 50% visible turbidity or the ATP level is inhibited.

Culture Media:

| | |
|---|---|
| NL 5082 | Mueller Hinton Broth |
| NL 5083 | Sabouraud-Dextrose Broth |
| NL 5425 | Brain-Heart Infusion |
| FCS | Foetal Bovine Serum |
| Tween 80 | Tween 80 |
| Agar | Agar No1 |

Test Strains:

| FH 6580 | ATCC 29213 | DSM 2569 | *Staphylococcus aureus* |
|---|---|---|---|
| FH 6495 | ATCC 25922 | DSM 1103 | *Escherichia coli* |
| FH 6585 | ATCC 29212 | DSM 2570 | *Enterococcus faecalis* |
| FH 6582 | ATCC 12344 | DSM 20565 | *Streptococcus pyogenes* |
| FH 2173 | — | — | *Candida albicans* |
| FH 6498 | ATCC 607 | DSM 43465 | *Mycobacterium smegmatis* |

The test strains were stored in Cryobank™ at −80° C.

Compound stock solutions were prepared at concentrations of at least 1000μg/ml with methanol. After testing, the stock solution is aliquoted and stored at −80° C. Nystatin was dissolved in DMSO and then further dissolved in the respective culture medium.

Preparation of Compound Dilutions (Serial Dilution) and Test Volumes:

For every test strain following controls on each 384 well clear-transparent microtitration plate are needed:
drug-free growth control,
sterile control, and
Ciprofloxacin and Nystatin as reference compounds.

For *Mycobacterium smegmatis* a special 384 well white microtitration plate was used.

For an $IC_{50}$ determination at least ten or twenty serial dilutions (geometrical dilution with factor 2) were prepared.

The broth media are described in the following Table 4:

| Broth Medium | Incubation Time | Strain | |
|---|---|---|---|
| NL 5082 | 20 h | FH 6580 | *Staphylococcus aureus* |
| NL 5082 | 20 h | FH 6495 | *Escherichia coli* |
| NL 5082 + 10% FCS | 20 h | FH 6585 | *Enterococcus faecalis* |
| NL 5082 + 10% FCS | 20 h | FH 6582 | *Streptococcus pyogenes* |
| NL 5082 | 20 h | FH 2173 | *Candida albicans* |
| NL 5082 | 48 h | FH 6498 | *Mycobacterium smegmatis* |

The usual test concentrations range from 64 to 0.125μg/ml or 64 to 0.0001μg/ml for strong inhibition. At the specification of the concentration the inoculation volume has to be considered. The whole test volume (compound solution and inoculum) was prepared with 40μl and accordingly for *Mycobacterium smegmatis* 20μl. The serial dilutions with Ciprofloxacin and Nystatin were prepared in special 384 well clear-transparent microtitration plate and were transferred in each 384 well microtitration plate before inoculation.

The inoculum has to be prepared from liquid precultures according to the following Table 5:

| Preculture | Incubation Time | | Strain |
|---|---|---|---|
| NL 5082 | 24 h | FH 6580 | *Staphylococcus aureus* |
| NL 5082 | 24 h | FH 6495 | *Escherichia coli* |
| NL 5082 + 10% FCS | 24 h | FH 6585 | *Enterococcus faecalis* |

-continued

| Preculture | Incubation Time | | Strain |
|---|---|---|---|
| NL 5082 + 10% FCS | 24 h | FH 6582 | *Streptococcus pyogenes* |
| NL 5083 | 24 h | FH 2173 | *Candida albicans* |
| NL 5425 + 1% Tween 80 | 48 h | FH 6498 | *Mycobacterium smegmatis* |

The preculture was prepared with one bead from Cryobank™ in 30 ml medium and incubated at 37° C., 180 rpm. The inoculum was adjusted by photometer at a wavelength of 590 nm and corresponds to $10^8$ CFU/ml. After adjustment the suspension was diluted to 1:100 for each strain, apart from *Mycobacterium smegmatis* 1:10,000. Within 15 minutes after inoculum preparation the microtitration plates were inoculated. The exact colony number of each strain was determined by a surface culture method.

Incubation: The inoculated microtitration plates were closed with lids, protected against evaporation, and incubated in an incubator at 37° C. in 5% $CO_2$, 95% atmospheric moisture for 20 h and for *Mycobacterium smegmatis* for 48 h.

Reading: The reading of the grown wells was done by means of a photometer for microtitration plates at 590 nm by absorbance mode. For *Mycobacterium smegmatis* the microtitration plates were measured by luminescence mode after incubation with 20μl BacTiter-Glo™/well for 5 minutes at room temperature protected from light.

Evaluation: The $IC_{50}$ values were determined in XLfit 4, model function 205. Results of the cell proliferation tests are reported in Table 6.

TABLE 6

$IC_{50}$ values of exemplified compounds [μg/mL]

| Strain [Assay mode: [1] Lum., [2] Abs.] | Compound | | |
|---|---|---|---|
| | (II) | (III) | (IV) |
| *M. smegmatis* (ATCC 607)[1] | 0.40 | 0.26 | 0.09 |
| *S. aureus* (ATCC 29213)[2] | 0.08 | 0.05 | 0.005 |
| *S. aureus* (ATCC 33592)[2] | 0.03 | 0.02 | 0.003 |
| *E. faecalis* (ATCC 29212)[2] | 0.87 | 0.59 | 0.07 |
| *S. pneumoniae* (DSMZ 11865)[1] | 0.28 | 0.34 | 0.21 |
| *S. pyogenes* (ATCC 12344)[2] | 0.28 | 0.12 | 0.04 |

The invention claimed is:

1. A compound of formula (I),

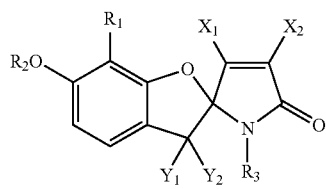

wherein
$R_1$ is $(C_6-C_7)$alkyl,
$R_2$ is H, $(C_1-C_6)$alkyl, or $(C_1-C_6)$alkylene-OH, $R_3$ is H or $(C_1$-$C_6)$alkyl, $X_1$ is selected from halogen, O—$(C_1$-$C_6)$alkyl, NH[$(C_1$-$C_6)$alkyl], NH[$(C_1$-$C_4)$alkylene-$(C_6$-$C_{10})$-aryl], NH[$(C_1$-$C_4)$alkylene-$(C_6$-$C_{10})$-heteroaryl], and S—$(C_1$-$C_4)$alkylene-N[$(C_1$-$C_4)$alkyl]$_2$, $X_2$ is halogen, and $Y_1$ and $Y_2$ are independently selected from H; OH; NH[$(C_1$-$C_6)$alkyl]; NH[$(C_1$-$C_4)$alkylene-$(C_6$-$C_{10})$-aryl], wherein the $(C_6$-$C_{10})$-aryl group is optionally substituted by halogen;

NH[$(C_1$-$C_4)$alkylene-$(C_6$-$C_{10})$-heteroaryl]; and a saturated or unsaturated heterocyclic ring system containing 5 to 6 ring atoms optionally substituted by $(C_1$-$C_6)$alkyl, wherein one or two ring atoms are selected from N, O, and S; or $Y_1$ and $Y_2$ together are =O, or a physiologically tolerated salt of a compound of the formula (I).

2. A compound of formula (I) according to claim 1, wherein $R_1$ is selected from n-hexyl, 4-methyl-pentyl, n-heptyl, and 4-methyl-hexyl.

3. A compound of formula (I) according to claim 1, wherein $R_2$ is selected from H, $(C_1$-$C_4)$alkyl, and $(C_1$-$C_4)$alkylene-OH.

4. A compound of formula (I) according to claim 1, wherein $R_3$ is H or $(C_1$-$C_4)$alkyl.

5. A compound of formula (I) according to claim 1, wherein $X_1$ is selected from Cl, Br, O—$(C_1$-$C_4)$alkyl, NH[$(C_1$-$C_4)$alkyl], NH[$(C_1$-$C_4)$alkylene-pyridyl], and S—$(C_1$-$C_4)$alkylene-N[$(C_1$-$C_4)$alkyl]$_2$.

6. A compound of formula (I) according to claim 1, wherein $X_1$ and $X_2$ are independently selected from Cl and Br.

7. A compound of formula (I) according to claim 1, wherein $X_1$ and $X_2$ are both Cl.

8. A compound of formula (I) according to claim 1, wherein $Y_1$ and $Y_2$ are independently of each other selected from the group consisting of H; OH; NH[$(C_1$-$C_6)$alkyl]; NH—$CH_2$-phenyl wherein the phenyl group is optionally substituted by halogen; and a saturated heterocyclic ring system containing 5 to 6 ring atoms optionally substituted by $(C_1$-$C_6)$alkyl; or $Y_1$ and $Y_2$ are together =O.

9. A compound of formula (I) according to claim 1, wherein $R_1$ is $(C_6$-$C_7)$alkyl, $R_2$ is H, $(C_1$-$C_4)$alkyl, or $(C_1$-$C_4)$alkylene-OH, $R_3$ is H or $(C_1$-$C_4)$alkyl, $X_1$ is halogen, O—(C1-C4)alkyl, NH[$(C_1$-$C_6)$alkyl], NH[$(C_1$-$C_4)$alkylene-heteroaryl] or S—$(C_1$-$C_4)$alkylene-N[$(C_1$-$C_4)$alkyl]$_2$, $X_2$ is halogen, and $Y_1$ and $Y_2$ are independently of each other selected from H; OH; NH[$(C_1$-$C_6)$alkyl]; NH—$CH_2$-phenyl wherein the phenyl group is optionally substituted by halogen; and a saturated heterocyclic ring system containing 5 to 6 ring atoms optionally substituted by $(C_1$-$C_6)$alkyl; or $Y_1$ and $Y_2$ together are =O, or a physiologically tolerated salt of a compound of the formula (I).

10. A compound of formula (I) according to claim 1, wherein $R_1$ is $(C_6$-$C_7)$alkyl, $R_2$ is H, $(C_1$-$C_4)$alkyl, or $(C_1$-$C_4)$alkylene-OH, $R_3$ is (C1-C4)alkyl, $X_1$ is selected from Cl, Br, NH[$(C_1$-$C_4)$alkyl], NH[$(C_1$-$C_4)$alkylene-pyridyl], and S—$(C_1$-$C_4)$alkylene-N[$(C_1$-$C_4)$alkyl]$_2$, $X_2$ is Cl or Br, and $Y_1$ and $Y_2$ are independently selected from H and OH, or $Y_1$ and $Y_2$ are together =O, or a physiologically tolerated salt thereof.

11. A compound of formula (I) according to claim 1, wherein $R_1$ is $(C_6$-$C_7)$alkyl, $R_2$ is H, $(C_1$-$C_2)$alkyl, or $(C_1$-$C_2)$alkylene-OH, $R_3$ is methyl, $X_1$ is selected from Cl, Br, NH[butyl], NH[$CH_2$-pyridyl], and S-ethylene-N[$(C_1$-$C_2)$alkyl]$_2$, $X_2$ is Cl or Br, and $Y_1$ and $Y_2$ are independently selected from H and OH, or $Y_1$ and $Y_2$ are together =O, or a physiologically tolerated salt thereof.

12. A compound of formula (I) according to claim 1, wherein $R_1$ is $(C_6$-$C_7)$alkyl, $R_2$ is H, $R_3$ is methyl, $X_1$ and $X_2$ are independently selected from Cl and Br, $Y_1$ and $Y_2$ are together =O, or a physiologically tolerated salt thereof.

13. A compound of formula (I) according to claim 1, wherein $R_1$ is $(C_6$-$C_7)$alkyl, $R_2$ is H, $R_3$ is methyl, $X_1$ and $X_2$ are both Cl, $Y_1$ and $Y_2$ are together =O, or a physiologically tolerated salt thereof.

14. A process for preparing a compound of formula (I)

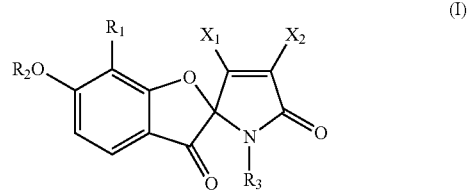

wherein $R_1$ is $(C_6$-$C_7)$alkyl, $R_2$ is H, $(C_1$-$C_6)$alkyl, or $(C_1$-$C_6)$alkylene-OH, $R_3$ is H or $(C_1$-$C_6)$alkyl, $X_1$ is selected from halogen, O—(C NH[$(C_1$-$C_6)$alkyl], NH[$(C_1$-$C_4)$alkylene-$(C_6$-$C_{10})$-aryl], NH[$(C_1$-$C_4)$alkylene-$(C_6$-$C_{10})$-heteroaryl], and S—$(C_1$-$C_4)$alkylene-N[$(C_1$-$C_4)$alkyl]$_2$, $X_2$ is halogen, and $Y_1$ and $Y_2$ are independently selected from H; OH; NH[$(C_1$-$C_6)$alkyl]; NH[$(C_1$-$C_4)$alkylene-$(C_6$-$C_{10})$-aryl] wherein the $(C_6$-$C_{10})$-aryl group is optionally substituted by halogen;

NH[$(C_1$-$C_4)$alkylene-$(C_6$-$C_{10})$-heteroaryl]; and a saturated or unsaturated heterocyclic ring system containing 5 to 6 ring atoms optionally substituted by $(C_1$-$C_6)$alkyl wherein one or two ring atoms are N, O or S; or $Y_1$ and $Y_2$ are together =O, or a physiologically tolerated salt of a compound of the formula (I), the method comprising:

1. fermenting the strain *Streptomyces* sp. ST 108140 (DSM 19369), or one of its variants and/or mutants, under suitable conditions in a culture medium until one or more of the compounds of the formula (I) accrue(s) in the culture medium,
2. isolating a compound of the formula (I) from the culture medium, and
3. derivatizing the isolated compound of the formula (I) to a compound of the formula (I), where appropriate, and/or, where appropriate, converting the isolated or derivatized compound into a physiologically tolerated salt of a compound of the formula (I).

15. A pharmaceutical composition comprising at least one compound of formula (I) or of a physiologically tolerated salt thereof according to claim 1.

16. A method for the treatment of an infection in a subject, the method comprising administering to said subject an effective dosage of a compound of the formula (I) or a physiologically tolerated salt thereof according to claim 1, wherein said infection results from a pathogen selected from *Staphylococcus aureus, Escherichia coli, Enterococcus faecalis, Streptococcus pyogenes, Candida albicans*, and *Mycobacterium smegmatis*.

17. A method for the treatment of an infection in a subject, the method comprising administering to said subject an effective dosage of a compound of the formula (I) or a physiologically tolerated salt thereof according to claim 1, wherein said infection results from a Gram-positive pathogen selected from Streptococci, Staphylococci, and Enterococci.

18. The method of claim 17, wherein said Gram-positive pathogen is selected from *Staphylococcus aureus, Enterococcus faecalis*, and *Streptococcus pyogenes*.

* * * * *